United States Patent [19]

Parkinson et al.

[11] 4,298,595

[45] Nov. 3, 1981

[54] PHARMACEUTICAL PREPARATIONS CONTAINING A POLYMERIC AGENT FOR RELEASING 5-AMINOSALICYLIC ACID OR ITS SALTS INTO THE GASTROINTESTINAL TRACT

[75] Inventors: Thomas M. Parkinson; Joseph P. Brown; Robert E. Wingard, Jr., all of Palo Alto, Calif.

[73] Assignee: Dynapol, Palo Alto, Calif.

[21] Appl. No.: 95,411

[22] Filed: Nov. 29, 1979

Related U.S. Application Data

[62] Division of Ser. No. 971,609, Dec. 20, 1978, Pat. No. 4,190,716.

[51] Int. Cl.$^3$ ............................................ A61K 31/74
[52] U.S. Cl. ...................................................... 424/78
[58] Field of Search .......................................... 424/78

[56] References Cited

U.S. PATENT DOCUMENTS 3,862,312  1/1975  Rimington et al. .................. 424/78

*Primary Examiner*—Frederick E. Waddell
*Attorney, Agent, or Firm*—William H. Benz; Thomas E. Ciotti; Norman H. Stepno

[57] ABSTRACT

An intestinal anti-inflammatory preparation comprising a polymeric agent for releasing 5-aminosalicylic acid or its salts is disclosed. The polymeric agent comprises a nonabsorbable pharmacologically acceptable organic polymer backbone containing aromatic rings to which are covalently bonded via azo bonds a plurality of salicylic acid or salicylate salt groups. The azo bonds attach to the salicylates' 5-position carbon. The polymer's azo bonds undergo bacterial cleavage in the mammalian lower bowel to release 5-aminosalicylic acid and/or its salts.

38 Claims, No Drawings

PHARMACEUTICAL PREPARATIONS CONTAINING A POLYMERIC AGENT FOR RELEASING 5-AMINOSALICYLIC ACID OR ITS SALTS INTO THE GASTROINTESTINAL TRACT

This application is a division of U.S. Ser. No. 971,609, filed on Dec. 20, 1978 and issued on Feb. 26, 1980 as U.S. Pat. No. 4,190,716.

BACKGROUND OF THE INVENTION

1. Field of the Invention

This invention concerns a pharmaceutical dosage form that contains a polymeric compound which, when ingested by a mammal, undergoes reaction with gastrointestinal bacteria to release an intestinal anti-inflammatory agent.

2. The Prior Art

Salicylazosulfapyridine (SASP)

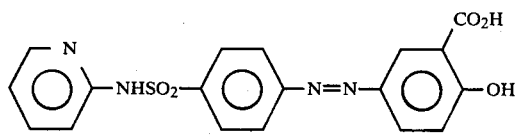

has been shown to be the most effective of the various sulfonamides in the treatment of ulcerative colitis and has been used in pharmaceutical preparations for over 30 years.

Upon oral ingestion, roughly 30% of the intact drug is directly absorbed from the upper small intestine. The remainder (~70%) suffers reductive azo cleavage in the caecum to give sulfapyridine (SP) and 5-aminosalicylic acid (5-ASA).

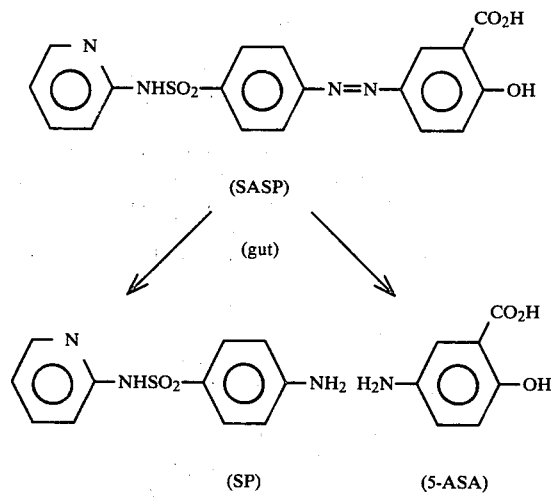

Absorbed SASP undergoes enterohepatic circulation and eventually is cleaved in the colon. Two to ten percent is excreted intact in urine. Sulfapyridine is absorbed, distributed throughout the body, and excreted in urine as glucuronide conjugates. Approximately 30% of the 5-ASA is absorbed from the colon; the remainder is excreted in the feces.

A limitation to the use of SASP is development of adverse side effects, which can be gastrointestinal (nausea, vomiting, anorexia, abdominal discomfort), hematologic (hemolytic anemia, leukopenia, transient reticulocytosis, pacytopenia), or generalized (headaches, vertigo, rashes, fever, cyanosis). In addition to these relatively common side effects, more serious adverse reactions have also been reported in the medical literature. These include agranulocytosis, toxic epidermal necrolysis, paresthesia, pancreatitis and pulmonary disease.

The toxic symptoms ascribed to SASP have been correlated with high serum concentrations of SP (>50 μg/ml) and decreased ability to acetylate SP. No correlation was observed with serum concentrations of SASP, SP metabolites, or 5-ASA.

The therapeutic mechanism of SASP could, in theory, be related to the intact drug or to either the antibacterial (SP) or antiinflammatory (5-ASA) cleavage product. In a recent study reported by A. K. Azad Kahn, et al., Lancet, 8044 (2), 892–5 (1977), and expanded upon by P. Sharon, et al., Gastroenterology, 75, 638–40 (1978), patients with ulcerative colitis were administered enemas of SASP and the two azocleavage products. About 75% of those who received SASP or 5-ASA improved, while only 38% of those who received SP showed a similar change. This significant difference, supported by sigmoidoscopy and biopsy findings, strongly suggests that 5-ASA is the therapeutic agent.

Assuming this hypothesis correct, we have reasoned that the toxic sulfapyridine portion of SASP merely serves to minimize intestinal absorption until 5-ASA can be generated by colonic bacterial reduction. A pharmaceutical dosage form containing a polymer leashed form of 5-ASA would be expected to be more effective than SASP for the site-specific release of 5-ASA in the colon. The potential advantages of the polymeric drug include nonabsorption in the small intestine (i.e., controlled release) and elimination of side effects caused by SP.

STATEMENT OF THE INVENTION

We have now discovered a new pharmaceutical agent comprising a polymeric compound which by its nature permits the prolonged administration of 5-ASA at a controlled rate while eliminating the release of undesired SP. This polymer compound is composed of a pharmacologically acceptable nonmetabolizable organic polymer backbone to which is attached a precursor of 5-ASA. The backbone has aromatic carbon atoms and is of a molecular size which precludes its absorption from the intestinal lumen. The 5-ASA precursor is an azo-linked salicylic acid or salicylate salt. These acid or salt groups are attached to the backbone through an azo linkage between a backbone aromatic carbon and a 5-position carbon on the salicylic acid or salicylate. When the polymer passes through the mammalian G.I. tract, the azo linkages are bacterially cleaved releasing 5-ASA. The generation of 5-ASA occurs in the lower bowel where its therapeutic action is desired. The backbone polymer itself passes through the gut, substantially intact and unabsorbed.

It is another aspect of this invention to provide a pharmaceutical formulation comprising such a polymer compound in combination with a pharmaceutically acceptable carrier. In yet another aspect the present invention provides a method of making a pharmaceutical formulation by admixing such a polymer compound with a carrier by known techniques. In a still further aspect, the present invention provides a method for delivery to a mammal a therapeutically effective amount of 5-ASA by orally or rectally administering to said mammal a pharmaceutical formulation comprising the present polymeric compounds. Such a delivery of 5-ASA is particularly effective for the treatment of intestinal inflammation, especially colitis and in particular ulcerative colitis which treatment is another aspect of this invention.

DETAILED DESCRIPTION OF THE INVENTION

Definitions

In the present description and claims, reference will be made to several terms which are expressly defined as follows:

The term "pharmacologically acceptable organic polymer backbone" shall mean a polymer backbone which is devoid of structural groups or atoms which are toxic or give rise to an adverse physiological response in mammals when ingested.

The terms "pharmaceutically acceptable organic polymer backbone" shall have the same meaning. Similarly, the terms "pharmaceutically acceptable" and "pharmacologically acceptable", when used to describe salts, cations, carriers, or the like, shall have the same meaning and shall mean a material which is devoid of groups which are toxic or give rise to an adverse physiological response in mammals when ingested.

The term "average molecular weight" shall designate a mean molecular weight as determined by gel permeation chromatography comparison with known standard molecular weight polymers.

The term "molecular size which precludes absorption through the intestinal lumen" shall mean a molecular size that is larger than the maximum molecular size which can readily pass through the mammalian intestinal wall.

The term "recurring" is used to describe repeating units in a polymer chain. As so used, the term is intended to encompass not only the situation wherein a single unit repeats in a "homopolymer" structure, but also the situation wherein a unit appears in a polymer chain interspersed with other different units in a "copolymer" structure.

Structure of the Polymeric 5-ASA Compounds

The compounds used in this invention are polymeric in nature and comprise salicylic acid groups (or salts thereof) bonded through their "5-carbon" position via azo links to aromatic carbons present in pharmacologically acceptable organic polymer backbones. Pictorially, such materials may be represented as shown in General Structural Formula

I.

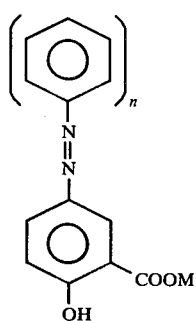

wherein M is hydrogen or a pharmacologically acceptable cation selected from among ammonium and the pharmacologically acceptable metal cations such as the nontoxic metal cations found in period 3, groups I, II and III; and period 4, groups I, II and VIII of the Periodic Table of the Elements, i.e., cations of Na, K, Cu, Mg, Ca, Zn, Fe, Co, Al and Ni. Preferably, M is hydrogen, or cations of Na or K so that the group is present as a salicylic acid group or as a sodium or potassium salicylate salt. Most preferably, M is sodium such that the group is a sodium salicylate group.

In pictorial representation I.

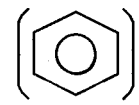

represents a portion of an aromatic-group-containing organic backbone from an aromatic carbon-atom of which extends an azo link and therefrom the salicylic acid or salicylate group. "n" is an integer that is greater than 1.

The Polymeric Backbones

The aromatic-group-containing polymer backbone may take either of two structures. In one, the aromatic groups are present as groups pendant from an organic chain which links them together into the desired polymer backbone. Such a structure has n recurring

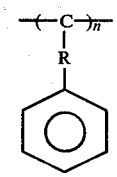

units wherein C is a portion of a nonmetabolizable organic chain linking the units together, n is an integer greater than 1 and R is a carbon to carbon single bond or a nonmetabolizable, pharmacologically acceptable organic linking group. Examples of such linking groups include amine links, sulfonamide links, ether links, ester links, amide links, carbamate links, alkyl links, and the like. Preferred as R are carbon-carbon single bonds and sulfonamide links.

The polymer backbones employed themselves are substantially nonmetabolizable (i.e., stable) under the conditions of the mammalian gastrointestinal tract and themselves do not break down into absorbable fragments under these conditions.

The second backbone aromatic group configuration which can be employed in the present polymeric compounds has the aromatic groups as integral part of the backbone; such a structure has recurring arylene units, i.e.,

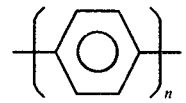

units. The azo links are attached to carbons of these arylene units. The backbones in either of these two configurations can be linear, branched or crosslinked so long as they present the requisite aromatic carbon groups required to affix the azo bonds in the final product. A number of examples of suitable polymeric backbones and an outline of the method of their use are given in a series of preferred embodiments. These are merely representative and are not to be construed as limiting the scope of the backbones useful in the practice of this invention. It is considered that the present invention involves the use of an overall molecular system for releasing 5-aminosalicylic acid, or its salts, and not merely a backbone. Accordingly, other art-known backbones which would provide the desired aromatic backbone carbons could be employed as well as the materials herein specifically embodied.

EMBODIMENT 1

Backbone: Polystyrene
Preparation:

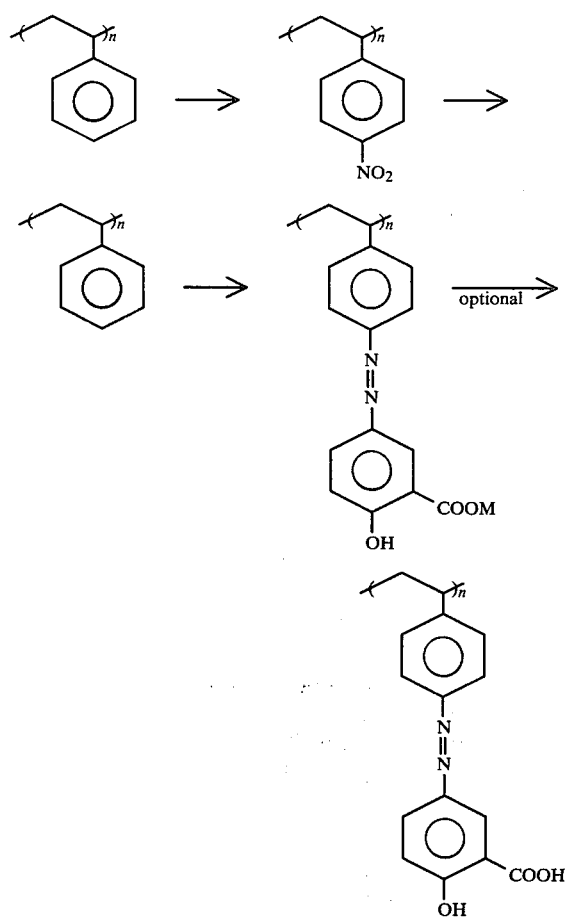

In this and all the other embodiments, only one polymer repeat unit is shown. This is done for simplicity. It will be appreciated that the several reactions may not be completely quantitative in yield. Accordingly, while the final product will have the unit shown as a recurring unit, it may also have minor amounts of other unreacted precursor units. In this embodiment, for example, the product might be expected to have four different units in an overall structure.

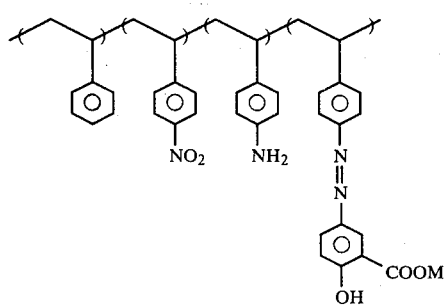

If, as is possible in accord with this invention, crosslinking groups were present, these would comprise a fifth recurring unit. It will be further appreciated that, since the salicylate-containing units contain the active species, it is generally desired to maximize the proportion of this unit and minimize the residual precursor units. Preferably, the salicylate-containing units make up at least 80% (more preferably from 90 to 100%) of the maximum number theoretically possible. (In other words, preferably at least 3 out of 4 backbone aromatic units carry an azo-linked salicylate group.)

The salicylate units in this and the other embodiments represent the active units. As such, in practice, it may be of importance to assay for their presence as well as for the presence of other units present in the polymer. Conventional analytical techniques known to the art will serve for these determinations. Representative analytical methods include the following:

Azo bond content is determined by reductive titration with chromous ion.

Salicylic Acid Moiety on polymer is determined by titration of carboxyl and phenol protons with tetrabutylammonium hydroxide in DMSO.

Aromatic Amine (on precursor polymer) is determined by redox titration with $NaNO_2$.

Aromatic Amide is determined by proton NMR using the methyl group proton signal for quantitation.

Aliphatic Amine is determined by a modified van Slyke method in which primary aliphatic amine is converted to $N_2$ gas. Measured volume of evolved $N_2$ is used to quantitate original amount of polymeric primary aliphatic amine.

EMBODIMENT 2

Backbone: Poly(vinylamine)*-Based Polysulfanilamide.
*Prepared such as by the method of U.S. Pat. No. 4,018,826.
Preparation:

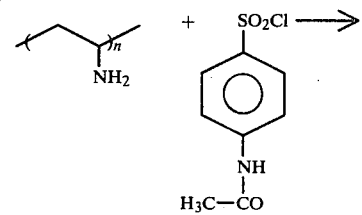

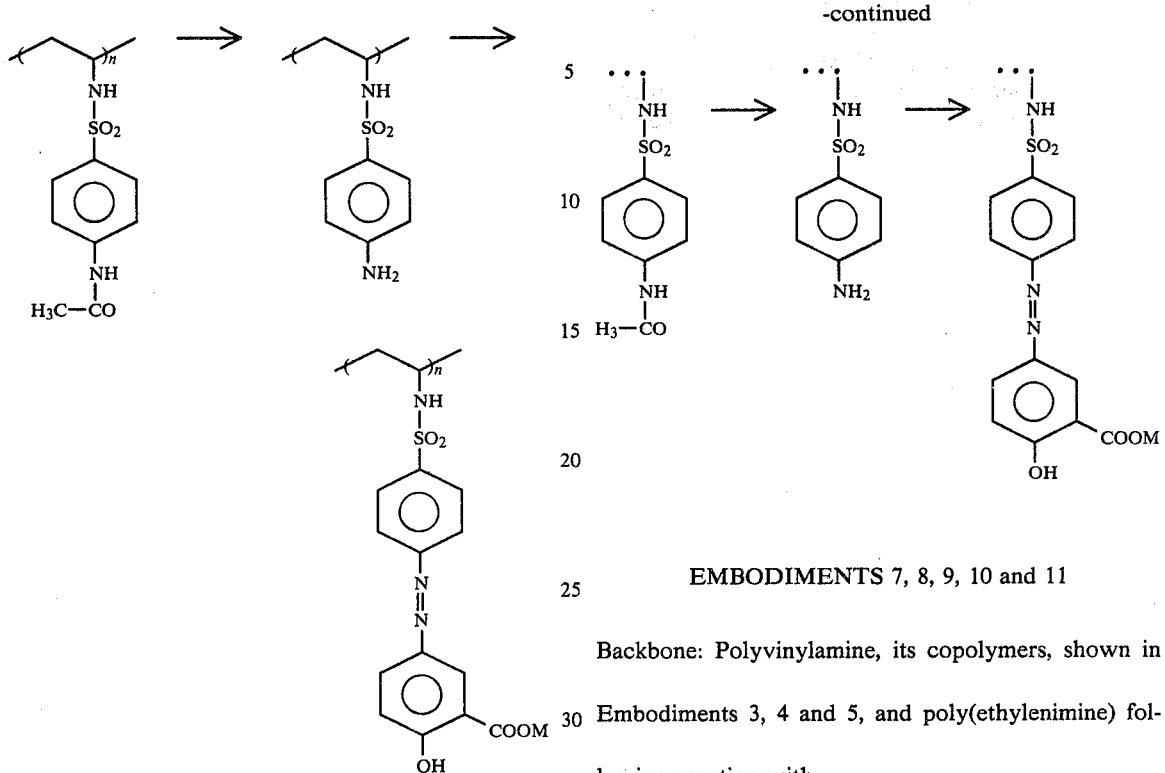

EMBODIMENTS 3, 4 and 5.

Backbone: The same as in Embodiment 2 except that the following units are copolymerized with the vinylamine units.

Embodiment 3—Acrylic acid (1–99 mole% basis number of total vinyl units). Such backbone materials and their preparation are shown in U.S. Pat. No. 3,920,855.

Embodiment 4—Vinyl sulfonate (1–99 mole% basis number of total vinyl units). Such copolymers and their preparation are shown in U.S. Pat. No. 4,096,134.

EMBODIMENT 6

Backbones: Poly(ethylenimine)-Based Polysulfanilamide.
Preparation:

EMBODIMENTS 7, 8, 9, 10 and 11

Backbone: Polyvinylamine, its copolymers, shown in Embodiments 3, 4 and 5, and poly(ethylenimine) following reaction with

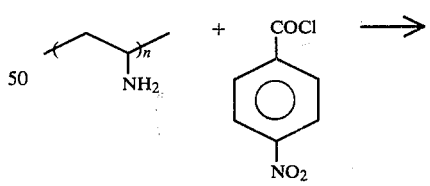

Aldrich Chemical
Cat. No. 11,220-8

Representative Preparation:

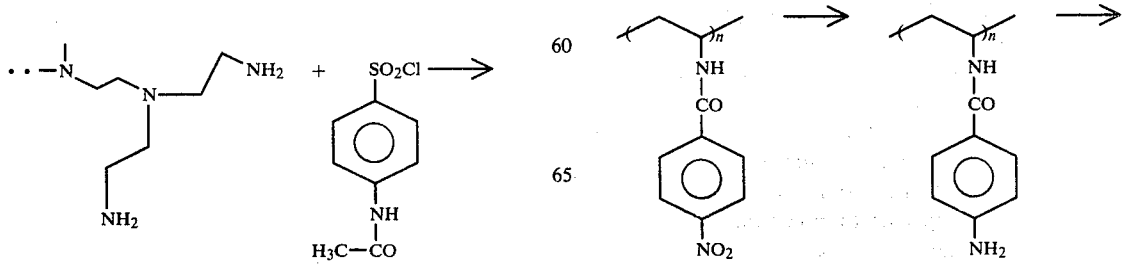

-continued

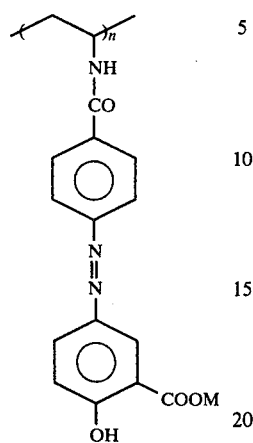

EMBODIMENTS 12, 13, 14, 15 AND 16

Backbone: Poly(vinylamine), its copolymers shown in Embodiments 3, 4 and 5, and poly(ethylenimine) following reaction with

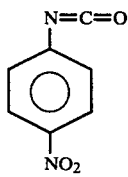

Representative preparation:

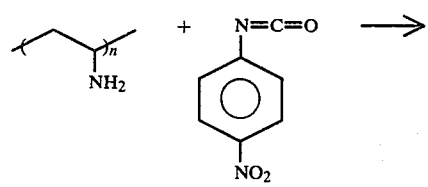

M. J. VanGelderen
Rec. Trav. Chim. Pays-Bas,
52, 1969, (1933).

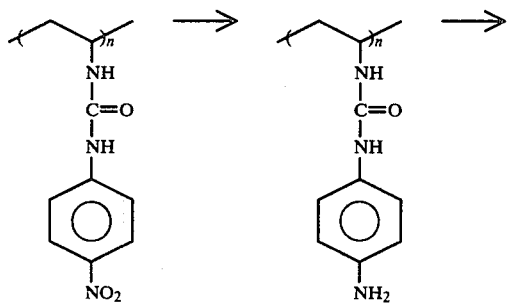

-continued

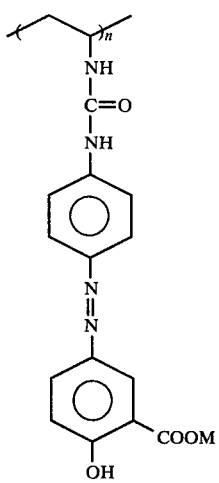

EMBODIMENTS 17, 18, 19, 20 AND 21

Backbone: Polyvinylamine, its copolymers shown in Embodiments 3, 4 and 5, and Poly(ethylenimine) following reaction with

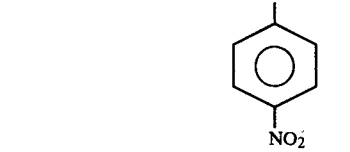

Representative Preparation:

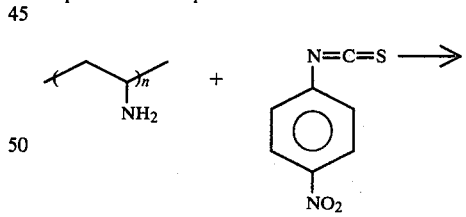

Eastman Organics
Catalog No. 9940

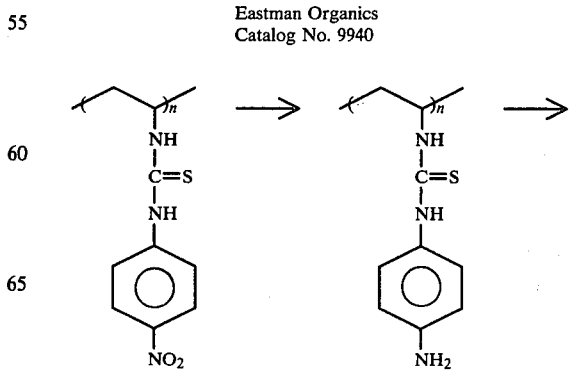

-continued

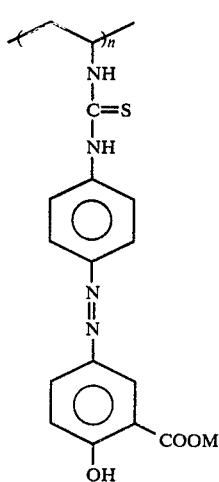

-continued

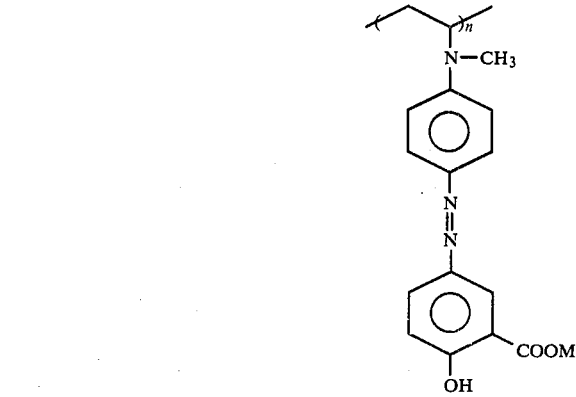

EMBODIMENT 22

Backbone: Poly(N-methylvinylamine) following reaction with

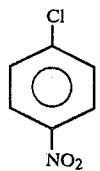

Preparation:

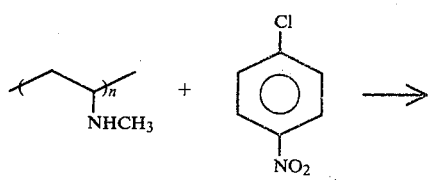

Aldrich, Cat. No. C5,912-2

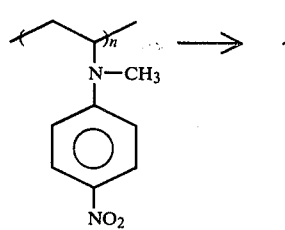 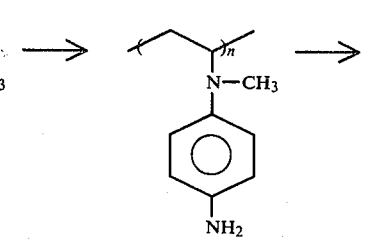

EMBODIMENT 23

Backbone use, instead of a homopolymer of N-methylvinylamine, a copolymer with from 1–99 mole % (basis total vinyl units) of ethylene, vinylsulfonate or acrylic acid.

EMBODIMENT 24

Backbone: Poly(vinyl alcohol) following reaction with

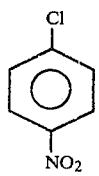

Preparation:

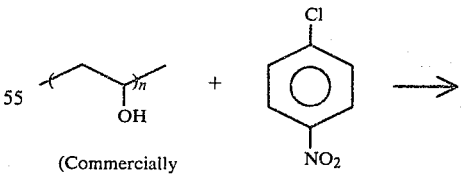

(Commercially Available)

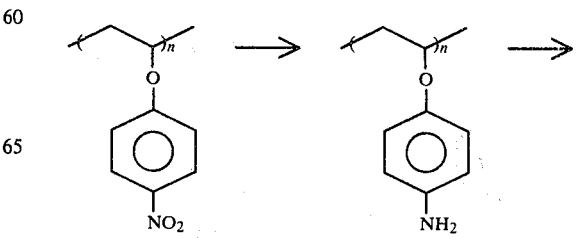

-continued
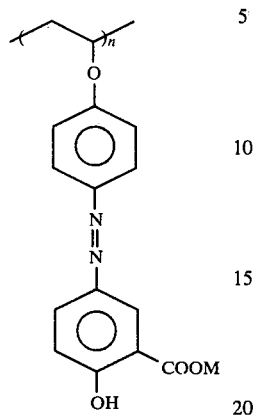
This same embodiment can also employ a copolymer of vinyl alcohol.
EMBODIMENT 25
Backbone: Poly(vinyl alcohol) (or copolymers of vinyl alcohol) following reaction with
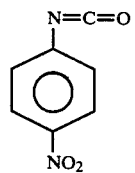
Preparation:
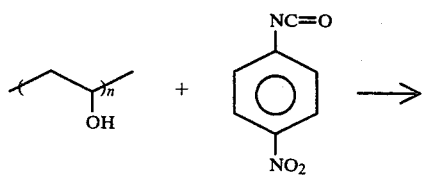
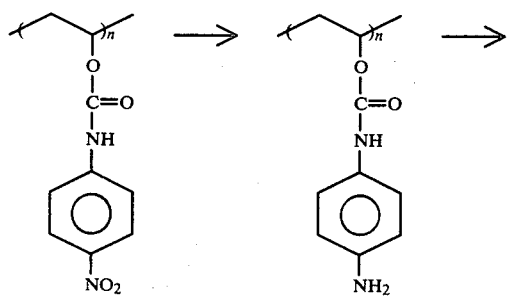
-continued
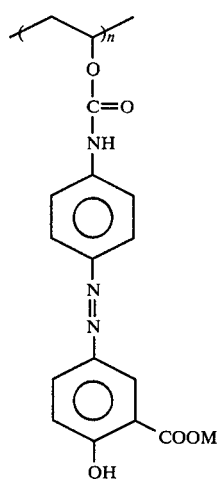
EMBODIMENT 26
Backbone: Poly(vinyl alcohol) or copolymers of vinyl alcohol following reaction with
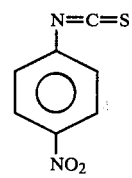
Preparation:
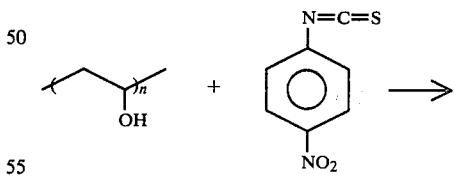
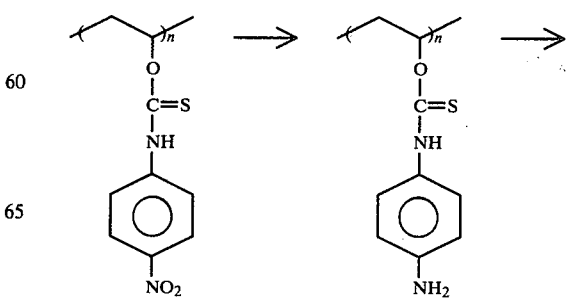

-continued
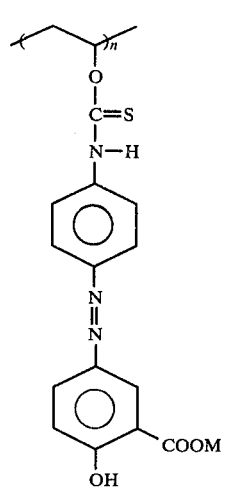
EMBODIMENT 27
Backbone: Poly(vinyl alcohol) or copolymers thereof following reaction with
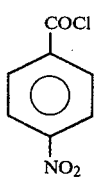
Preparation:
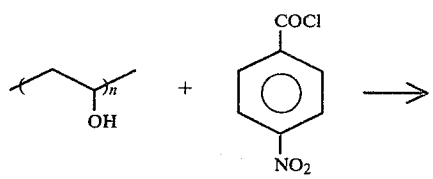
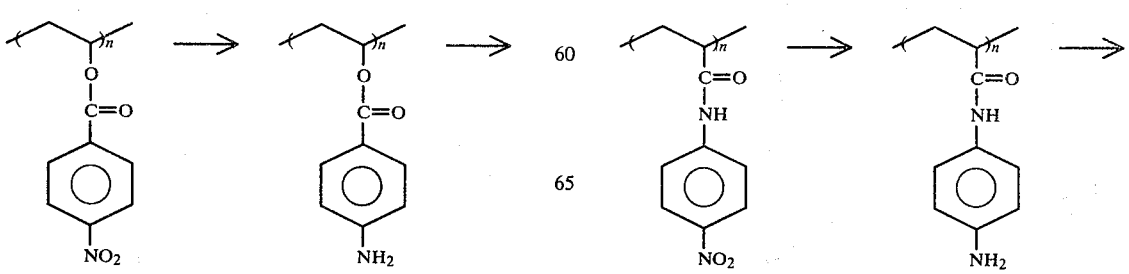
-continued
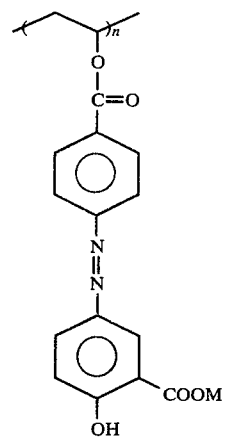
EMBODIMENT 28
Backbone: Poly(acryloyl chloride) following reaction with
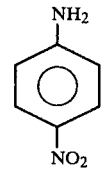
Preparation:
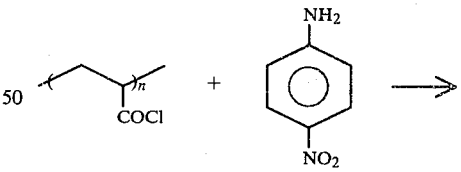
Aldrich, Cat. No. N985-3

-continued
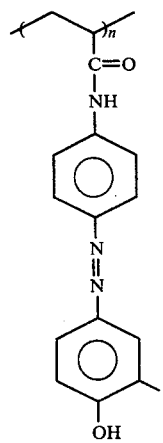
EMBODIMENT 29
Backbone: Poly(acryloyl chloride) following reaction with
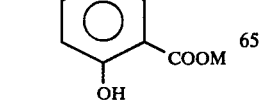
Preparation:
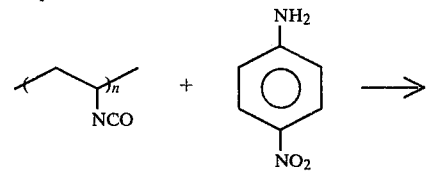
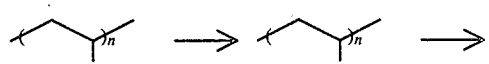
EMBODIMENT 30
Backbone: Poly(vinylisocyanate) following reaction with
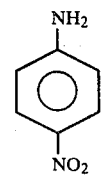
Preparation:
C. G. Overberger and C. J. Podsiadly,
Macromol. Synth., Coll. Vol. I,
John Wiley, N.Y., pp 473–476.
EMBODIMENT 31
Backbone: Poly(vinylisocyanate) following reaction with
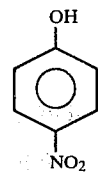

Preparation: This would be the same as the preparation shown in Embodiment 29 substituting poly(vinylisocyanate) as a starting material. The product would be

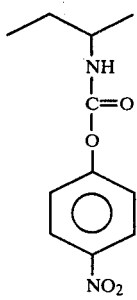

EMBODIMENT 32

Backbone: Poly(epichlorohydrin) following reaction with p-nitrophenol.
Preparation:

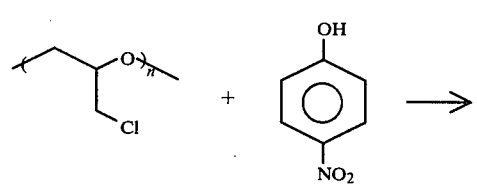

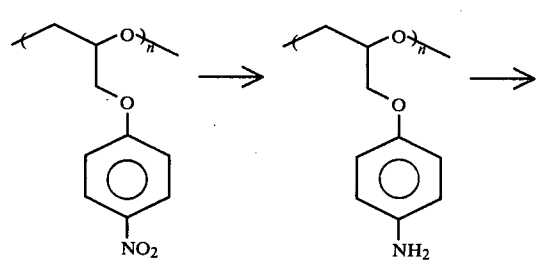

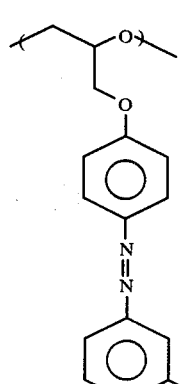

EMBODIMENT 33

Backbone: Poly(epichlorohydrin) following reaction with

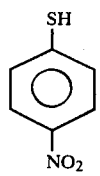

Preparation:

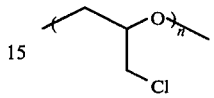 + 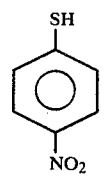 →

Aldrich,
Cat. No.
N2,720-9

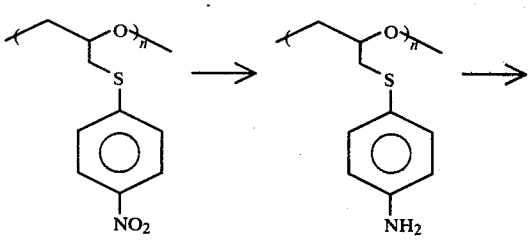

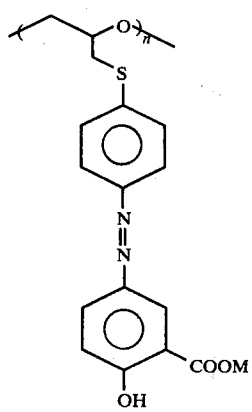

EMBODIMENT 34

Backbone: Poly(epichlorohydrin) following reaction with

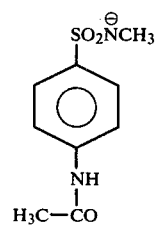

Preparation:

-continued
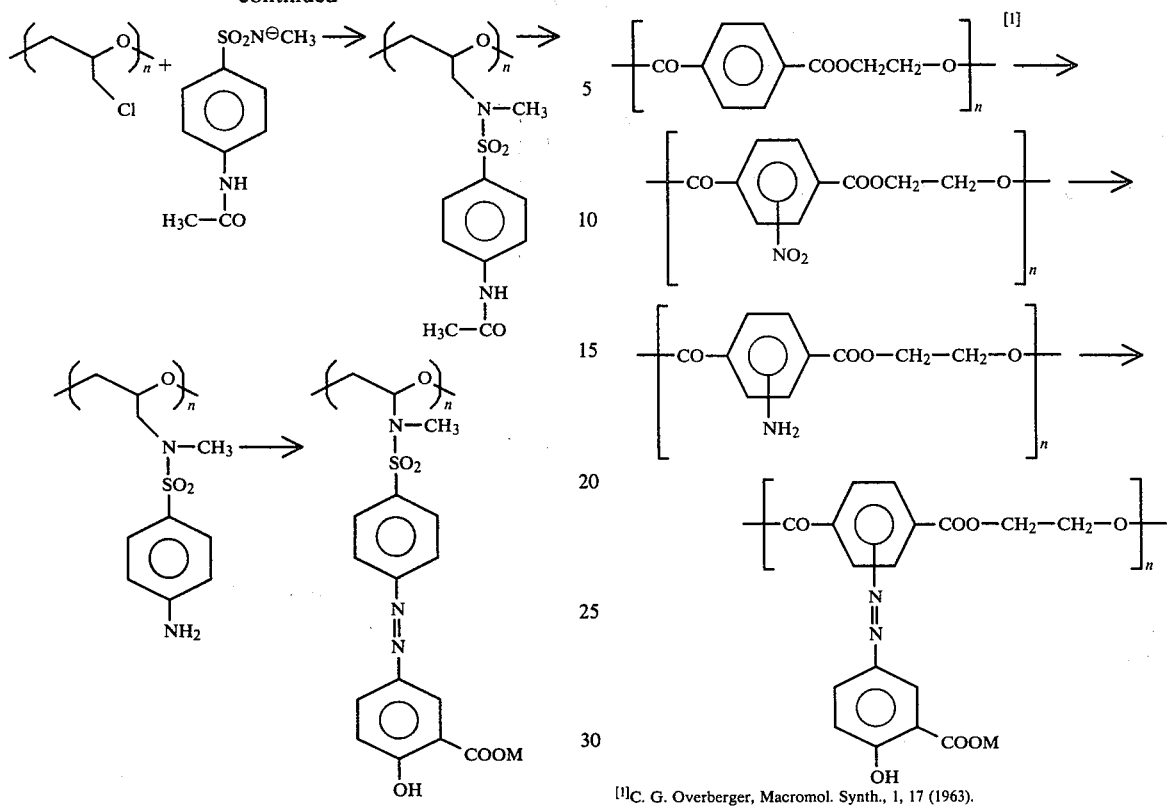
EMBODIMENT 35
Backbone: Poly(ethylene terephthalate)
Preparation:
EMBODIMENT 36
Backbone: Bisphenol-A Polycarbonate [1].
[1] C. G. Overberger, Macromol. Synth., 1, 9 (1963).
Preparation:
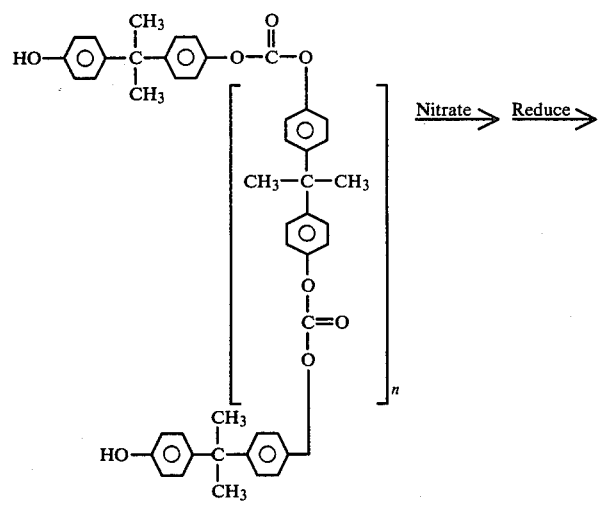

-continued
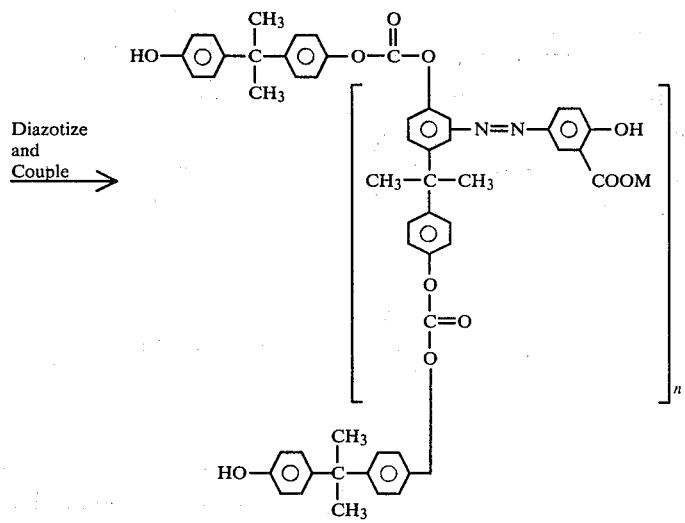
EMBODIMENT 37
Backbone: Bisphenol A Polysulfone
Preparation:
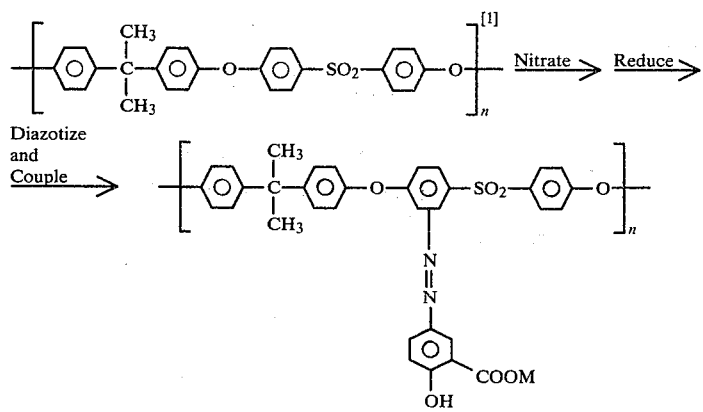
[1]Sorenson and Campbell, "Preparative Methods of Polymer Chemistry," 2nd Ed., Interscience, New York, N.Y., 1968, pp181-2.
EMBODIMENT 38
Backbone: Poly[2,2-propanebis(4-phenyl carbonate)]
Preparation:
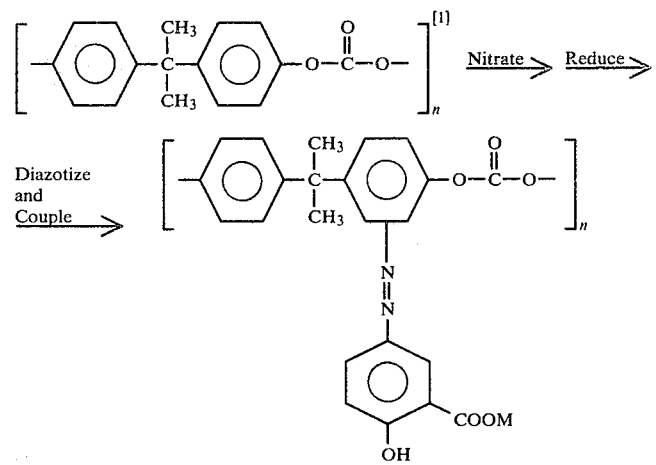
[1]Sorenson and Campbell, p 140-1.

Preferred Backbones

While there is no present reason to believe that certain backbones do a better or worse job of releasing the salicylates or salicylic acid into the gastrointestinal tract, some classes of backbones are preferred because of their ease of use in synthesis. For example, water-soluble backbones are generally easier to use, diazotize and couple than are water-insoluble backbones. Backbones based on alkylamine-group-containing polymers, especially those shown in Embodiments 2 through 6 are preferred. These materials are available and art-known, or based on available art-known precursors.

The molecular size of the backbone is important. If it is to accomplish its purpose of remaining nonabsorbable through the walls of the gastrointestinal tract, it must have a molecular weight above about 1000 daltons. Generally, this means that the backbone should have an average molecular weight of at least 1000 daltons with an average weight of from about 2000 to about 10,000,000 daltons being preferred and average molecular weights of from about 3,000 to about 1,000,000 daltons being more preferred and average molecular weights of from 5,000 to 500,000 being most preferred. If a polymer having a low average molecular weight is sought to be used, it may be of advantage to fractionate it, such as by fractional precipitation or ultrafiltration, so as to remove low polymers and oligomers having a molecular weight below about 1000 daltons. If a cross-linked polymer backbone is employed, an average molecular weight having orders of magnitude above those shown here would be realized, say in the many tens of millions.

These desired molecular weights also give rise to preferred value for n, the integer defining the number of units of salicylic acid on the polymer. As previously noted, n is at least 1. Preferably, n is from 5 to 40,000, with values of from 10 to 10,000 being more preferred.

The degree of substitution, that is the fraction of backbone aromatic rings that are substituted with azo-linked salicylic acid groups can vary. No advantage is seen in very low substitution as it means that exaggerated amounts of backbone need be consumed. Substitutions of from about 10 to 100% are generally preferred with increasingly more preferred ranges of substitution being 30 to about 100%; 50 to 100%, 80 to 100% and 95 to 100%. As a rule, only one azo group attaches to a single backbone aromatic ring. It is preferred if the number of backbone aromatic rings is 10 or greater and the number of salicylate units (n) is 5 or greater. More preferably, the number of rings is from 10 to 30,000 while n is from 5 to 20,000. Most preferably, the number of rings is 10 to 20,000 and n is 10 to 10,000.

Preparative Methods

In the illustrative embodiments, a variety of preparative methods are briefly set forth. The examples describe several methods in detail. In this section a general expansion of the methods of the illustrative embodiment is provided.

A. In Embodiments 1 and in many later embodiments, an azo group is introduced by (1) nitrating an aromatic ring, (2) reducing the resulting aromatic nitro group to an amine. In all embodiments diazotizing and coupling are shown. The nitration of aromatic rings may typically be carried out by standard methods such as those found in C. A. Buehler and D. E. Pearson, "*Survey of Organic Syntheses,*" Vol. I, Wiley-Interscience, New York, N.Y., 1970, pp 980–991. Preferred methods include the use of (1) $KNO_3$ in 96% $H_2SO_4$, (2) mixed acid ($HNO_3$-$H_2SO_4$), and (3) red fuming nitric acid.

The reduction of these nitro groups to amines may be conducted using standard procedures such as those found in C. A. Buehler and D. C. Pearson, "*Survey of Organic Syntheses,*" Vol. I, Wiley-Interscience, New York, N.Y., 1970, pp 413–417. Preferred methods include (1) treatment with $Na_2S$, (2) treatment with sodium dithionite ($Na_2S_2O_4$), (3) treatment with metal (e.g., Fe, Sn, or Zn) and acid, (4) catalytic reduction (e.g., 5% Pd on C and $H_2$), and (5) treatment with phenylhydrazine with sodium dithionite reduction being generally preferred.

The diazotization of the aromatic amine groups is carried out on an acidic solution or suspension of the polymers. The solution or suspension is contacted with a slight excess of a nitrite, such as sodium nitrite, potassium nitrite or the like at low temperatures (0° C. to about 35° C.). The diazotization is generally very quick, requiring only a minute or two so that reaction times of from 0.1 minute to about 2 hours may be used. If a relatively water-insoluble polymer is to be diazotized, this may be carried out in nonaqueous media. In such a reaction nitrosylchloride, nitrosyl bromide, alkyl nitrate esters or nitrosyl sulfonic acid or the like may be used in standard organic solvents such as lower alcohols or chlorinated hydrocarbons. This would be carried out at low temperatures.

The diazotization of the aromatic amine groups is carried out on an acidic solution or suspension of the polymers. The solution or suspension is contacted with a slight excess of a nitrite, such as sodium nitrite, potassium nitrite or the like at low temperatures (0° C. to about 35° C.). The diazotization is generally very quick, requiring only a minute or two so that reaction times of from 0.1 minute to about 2 hours may be used.

The coupling of the salicylic acid group is effected promptly after the amines are diazotized. The solution or suspension of diazotized polymer is mixed with a solution of salicylic acid at low temperature (0° C. to about 35° C., preferably 10° C. to 25° C.). Some excess of salicylic acid is generally employed. The pH is maintained basic, such as above about pH 10, preferably pH 13–13.5 by addition of base, such as KOH or NaOH. The mixing may be done stepwise. The time required for coupling is from about 0.25 hour to about 5 hours with times of 0.5 to 1.0 hours generally giving good results.

B. It has been pointed out that the salicylic acid group may be present as a free acid or as a salt. If the acid is desired, the coupling product is acidified with a strong acid such as hydrochloric acid or the like. If a salt is desired, acidification need not be carried out.

C. In preferred Embodiments 2–6, an alkylamine is converted into a sulfonamide group as the required pendant aromatic ring is introduced. This step is well effected by a "Schotten-Baumann" type reaction wherein the alkyl amine is contacted with an aromatic compound containing an amine precursor functionality and a sulfonyl chloride functionality

at relatively low temperatures (40° C. or less) and a pH of about 9-10. A typical reaction employs an aqueous reaction solvent, preferably also containing some water-miscible polar organic solvent such as tetrahydrofuran, dioxane, dimethoxyethane, diglyme, isopropanol, t-butanol or 2-methoxyethanol and vigorous agitation.

Suitable aromatic compounds for use herein are N-acetylsulfanilyl chloride,

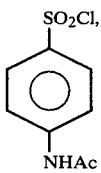

and the like.

The concentration of polyamine in the solution should be maintained at from about 1% to about 20%. As a rule, the aromatic compound should be added gradually over a period of at least about 0.25 hours. During this addition, the pH should be monitored and maintained between about pH 9 and 10. After the addition is completed, the pH may suitably be raised somewhat, such as to 10-11, and the mixture stirred for an additional 0.5 to 4 hours. The reaction which occurs is as follows in the case where N-acetylsulfanilyl chloride is employed:

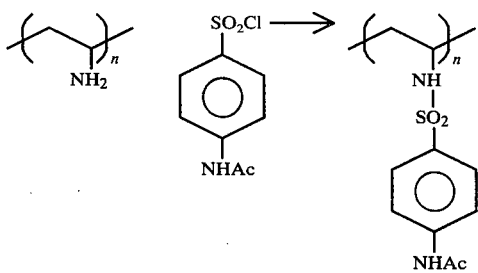

The product of this reaction may be isolated by stripping off the organic solvent and filtering. It is then contacted with acid (generally a substantial excess of aqueous mineral acid solution such as from 3-10 equivalents of acid per equivalent of acetyl groups) to deacetylate it. The deacetylation is not a rapid reaction, requiring about 6 hours at reflux temperatures (100° C.). Higher or lower temperatures (200° C. or 50° C.) could be used if desired with accompanying changes in reaction time. This deacetylation produces the polymer

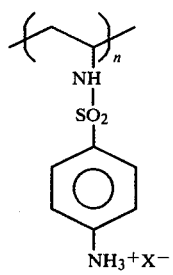

wherein $X^-$ is the anion corresponding to the mineral acid employed.

D. In Embodiments 7-11, the condensation of a polymeric amine with

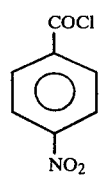

is shown. This reaction may be carried out by contacting the polyamine with an excess of the acid chloride in aqueous media of alkaline pH at moderate temperatures (roughly 0°-35° C.) for 0.5-3 hours.

E. In Embodiments 12-21 and 25 and 26, coupling reactions with

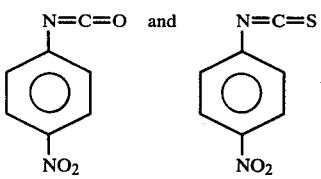

are shown. The polyamine couplings may be conducted with an excess of the isocyanate or the isothiocyanate in aqueous media at moderate temperatures (about 0°-35° C.) for 0.5-3.0 hours. The coupling reactions with polyvinyl alcohol are best conducted neat or in an inert solvent (e.g., dimethyl sulfoxide or hexamethylphosphoramide). These reactions also require higher temperatures and longer contact times.

Use of the Salicylic Acid Polymers

The salicylic acid polymers incorporated in the pharmaceutical composition of this invention have the property of undergoing bacterial cleavage of their azo bonds at conditions found in the lower intestinal tract of mammals. The 5-aminosalicylic acid molecular fragment so liberated thus is available to function as a therapeutic agent locally on the mucosa of the lower intestinal tract.

The polymer compounds of Formula I may be presented in association with a pharmaceutically acceptable carrier in pharmaceutical formulations suitable for oral or rectal administration. Suitable carriers include solids such as lactose, starch (pharmaceutical grade), dicalcium phosphate, calcium sulfate, kaolin, mannitol and powdered sugar and liquids.

The formulations for oral or rectal administration are advantageously presented in discrete unit dosage forms, such as tablets, capsules, cachets, suppositories, each containing a predetermined amount of each compound, but may also be presented as a powder, or as granules. They may as well be presented as a solution or suspension in an aqueous or non-aqueous liquid such as would be useful for oral or rectal administration. The formulations may be made by any of the known methods and may include one or more of the following accessory ingredients: buffers, flavoring, binding, dispersing, surface-active, thickening, lubricating and coating materials, preservatives, bacteriostats, antioxidants, suppository and ointment bases, coloring agents, and any other acceptable excipients. Unit dosage forms may typically contain from about 0.01 to about 1 gram of releasable 5-aminosalicylic acid.

Any skilled artisan can prepare these dosage forms by simply referring to the oral dosage form preparatory procedure outlined in "Remington's Pharmaceutical Sciences," Fourteenth Edition (1970), pages 1624 through 1698 inclusive, and the rectal dosage form preparatory procedure outlined in the same text at pages 1617 through 1624, inclusive.

The pharmaceutical compositions of this invention find application in the treatment of inflammations, especially intestinal inflammations such as colitis, in man and other mammalian species. These compositions are especially indicated in the treatment of ulcerative colitis. The therapeutic dosage range for compositions containing the present polymers will vary with the degree of substitution of the polymer with releasable 5-ASA units as well as the size and needs of the patient. With related monomeric compound, salicylazosulfapyridine (SASP) the maximum recommended dose for a 70 kg adult male is 8 g/day with 5 g/day being a preferred maximum. (These values are equivalent to 114 mg of SASP/kg of body weight/day and 71.4 mg/kg day or 0.29 and 0.18 mmoles of SASP/kg of body weight/day.) As previously noted, the present polymeric forms of 5-ASA serve to reduce or eliminate a number of side-effects observed with monomeric SASP. This means that, at least potentially, higher equivalent dosages might be employed. Accordingly, dosages of pharmaceutical compositions comprising the present polymers may range from about 0.03 to about 0.5 milliequivalents of releasable 5-ASA/kg of body weight per day with dosages of from about 0.05 to about 0.4 milliequivalents of releasable 5-ASA/kg/day being preferred. In any event, a therapeutically effective dose is to be employed.

The invention will be further described by the following examples. They are intended soley to exemplify the invention and are not to be construed as limiting its scope.

EXAMPLE I

Reaction Scheme:

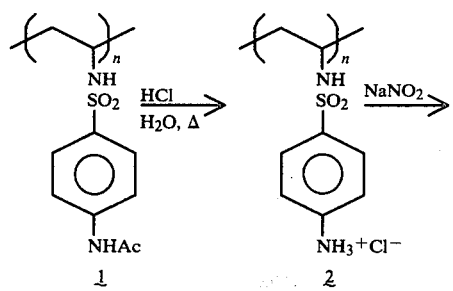

-continued

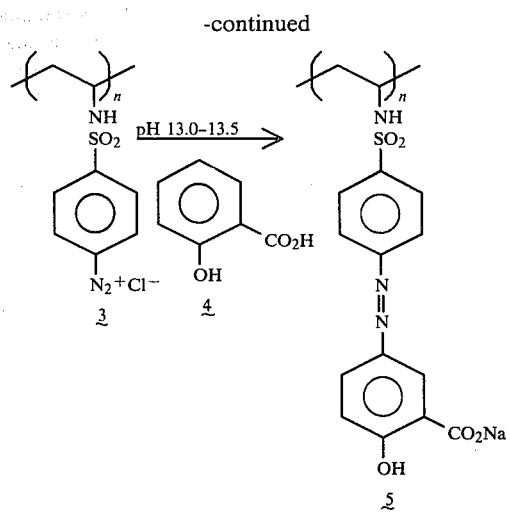

PRECURSOR PREPARATION

Precursor poloymer 1 was prepared using the procedure of Gless et al, U.S. Pat. No. 4,018,826 and JACS 98:19 (Sep. 15, 1976). In a typical preparation a 2-1., three-neck flask, equipped with an overhead stirrer, thermometer, and dry-ice condenser, was charged with 532 g (9.0 mol) of technical acetamide. With stirring, 12.4 ml of 6 M $H_2SO_4$ and 134 g (3.0 mol) of acetaldehyde were added sequentially and the reaction vessel was heated with a 100° C. oil bath. After the reaction had stirred for 10 min, the internal temperature ($T_i$) was 75° C. and the mixture was homogeneous. The condenser was removed as an exotherm began, which raised $T_i$ to 100° C. within 2 min. Ethylidene bisacetamide crystallized rapidly from the mixture, causing a further increase in $T_i$ to 108° C. After 7 min at or above 100° C., the heating bath was turned off and 60 g (0.60 mol) of $CaCO_3$ (precipitated chalk) was carefully added, followed by 30 g of Celite 503.

The reaction vessel was fitted with a wide-bore, vacuum-distillation apparatus equipped with a Vigreux column and the pressure was slowly decreased to 30–40 mmHg. The bath was heated to 200° C. and the mixture was distilled to dryness (~4 h).

The crude distillate was melted, diluted with 250 ml of isopropyl alcohol, and cooled to 5° C. for 18 h. Filtration afforded 125 g of acetamide and a filtrate which was 38.7 wt % N-vinylacetamide by bromine titration. This solution was subjected to polymerization without further purification.

A 5-1., four-neck flask, equipped with an overhead stirrer, thermometer, reflux condenser, Ar inlet, and heating mantle, was charged with 1165 g of an N-vinylacetamide solution (451 g, 5.30 mol) prepared as described in the preceding step. After isopropyl alcohol addition (1.3 1.), the reaction mixture was thoroughly deoxygenated and heated to a vigorous reflux under Ar. A solution of 22.3 g (0.14 mol) of AIBN in 83 ml of acetone was added in one portion and the reaction was refluxed for 3 h.

After cooling, most of the solvent was removed in vacuo and the resulting thick orange oil was precipitated by slow addition to 10 l. of rapidly stirred acetone. The solid was filtered, washed with acetone (3×2 1.), and dried in vacuo at 50° C. to afford 431 g (96%) of poly(N-vinylacetamide) as a white powder.

A 5-l., four-neck flask equipped with overhead stirrer, thermometer, distillation head, and heating mantle, was charged with 1 l. of H$_2$O and stirring was begun. The H$_2$O was boiled as 1412 g of an acetone-wet filter cake of polymer (424 g, 4.98 mol as determined by drying a sample, $M_p^{ps}3\times 10^4$) was added along with 200 ml of H$_2$O. After the acetone had been removed by distillation, the mixture was cooled and treated with 522 ml of 12 N HCl (6.26 mol). Reflux was resumed under Ar. At 40 h, the cloudy solution was treated with 100 ml of H$_2$O and precipitated, while still warm, into 14 l. of rapidly stirred isopropyl alcohol. The product, polyvinylamine hydrochloride, was filtered, washed with isopropyl alcohol (6 l.), and dried in vacuo to afford 415 g of an off-white powdery solid. A 1-l. flask was fitted with an overhead stirrer, a 100-ml dropping funnel containing 8 N NaOH, a pH probe, and a gas inlet tube. The vessel was charged with 14.0 g (176 mmol) of the poly(vinylamine hydrochloride), 140 ml of H$_2$O, 15 ml of 8 N NaOH, and 70 ml of THF. With vigorous stirring, 15.1 g (64.6 mmol) of powdered p-acetamidobenzenesulfonyl chloride was added and the pH was maintained at 9-10 by base addition as necessary for 5 min. A second portion of the sulfonyl chloride (15.1 g) was then added followed by 70 ml of THF. After an additional 15 min at pH 9-10, a third equal portion of the sulfonyl chloride was added followed by 70 ml of THF and the pH was maintained at 10-11 until no further reaction was observed (stable pH, 60 min).

The flask was equipped for vacuum distillation and the THF was removed (35° C. (20 mm)). Schotten-Baumann product $\underline{1}$ precipitated as an easily filterable, light-tan, brittle solid. The yield was 41.7 g (99%) after thorough water washing and drying.

By varying polymerization reaction conditions such as temperature and cosolvent, the molecular weight of the polymer can be varied.

A. Hydrolysis

A 100-ml, 3-neck flask, equipped with overhead stirrer and oil bath, was charged with 4.00 g (16.7 mmol) of polymer $\underline{1}$ (prepared as shown in the above Precursor Preparation on poly(N-vinylacetamide) of average molecular weight, as determined by GPC comparison with polystyrene standards, of $3\times 10^4$), 33 ml of H$_2$O and 8.80 ml (106 mmol) of 12 N HCl. The mixture was stirred vigorously at reflux for 6 hours to effect hydrolysis.

B. Diazotization and Coupling

The solution of polymeric sulfanilamide prepared above was converted to diazonium salt $\underline{3}$ by the rapid addition of 4.00 ml (20.0 mmol) of 5 N NaNO$_2$ solution via syringe (25° C., vigorous stirring). A positive KI starch test was obtained after 5 minutes.

A 600-ml beaker, fitted with magnetic stir bar, thermometer, pH probe, and 50-ml dropping funnel, was charged with 6.9 g (50.1 mmol) of salicylic acid (4), 200 ml of H$_2$O, and 12.5 ml (100 mmol) of 8 N NaOH. After stirring for 5 minutes, ice was added to the clear solution to lower the temperature to 10° C. and the addition of the diazonium salt (via the dropping funnel) was begun.

Throughout the addition (45 min) the pH was maintained at 13.0-13.5 by the addition of 8 N NaOH (16.5 ml added), and the temperature maintained at 10°-20° C. by the addition of ice. The solution was stirred for one hour at ambient temperature and then neutralized (to pH 7) by the addition of 12 N HCl.

The salts and low molecular weight impurities were removed by bag dialysis (regenerated cellulose, average pore radius 2.4 nm, estimated molecular weight cutoff $2\times 10^4$) against 0.05% saline solution for 168 hours (dialysate changed every 12 hours), followed by dialysis against pure H$_2$O for 12 hours. The solution was centrifuged (5000 rpm $\times$ 90 min) to remove a small amount of crosslinked product, passed through an 8.0$\mu$ filter, and freeze dried to afford 5.65 g (91.7%) of polymeric drug $\underline{5}$ as solid: UV $\lambda_{max}$ (H$_2$O) 354 nm, a 44.2 (g/L$^{-1}$cm$^{-1}$). Anal. Calcd for (C$_{15}$H$_{12}$N$_3$O$_5$SNa.2H$_2$O)$_n$: C,44.44;H,4.02;N,10.37;S,7.91. Found: C,44.40;H,4.06; N,10.13;5,7.84.

As previously explained, the pictorial depiction of product 5 is presented as a best representation of the polymer product. The repeat unit shown,

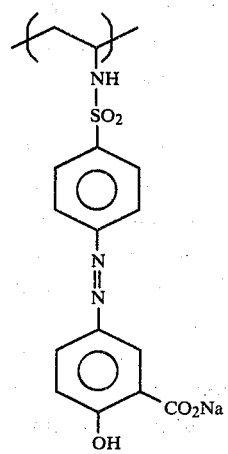

is by far the predominant species (well over 80% of the total weight of the product polymer, and generally over 90% by analysis). No other units are intentionally introduced, but it should be recognized that the product will probably contain minor amounts of units which either result from side reactions or incomplete reactions. For example, the poly(vinylacetamide) hydrolysis is often not quantitative. It is theorized that the small residum may be later hydrolyzed to aliphatic amines. Similarly, minor amounts of hydrolyzed amides may fail to couple in the Schotten-Baumann reaction. These groups might well diazotize to give unstable aliphatic diazonium salts which could react with water present to give an alcohol group, or with Cl$^-$ present to give an alkyl chloride group. Similarly, the hydrolysis of the attached acetanilide prior to diazotization may not be quantitative such that a small amount of residual aromatic amides are present. The fact that the primary unit is as shown is known with certainty. The possible presence of minor amounts of unintentionally incorporated co-units is suspected based on normal polymer chemistry. The proportions of these possible units may be determined as set forth above.

The reaction sequence of parts A and B was repeated several times varying the molecular weight of the poly(vinylamine hydrochloride) such as to $M_p^{ps}$ $1.2\times 10^5$ and varying the metal cation to potassium.

C. Biological Tests

A series of in vitro and in vivo tests were conducted to demonstrate the behavior of the polymer product of Part B in the mammalian gastrointestinal tract.

The polymer product of Part B was contacted with rat lower bowel microflora in vitro and observed to undergo anaerobic reductive azo bond cleavage.

Cecal contents were removed from a freshly sacrificed rat, suspended in VPI diluent and filtered under $N_2$. Five ml of the cell suspension (1 g fresh weight/25 ml) were added to 0.05 ml of 20 w% α-D-glucose, 0.5 ml 1.0 mM benzylviologen or distilled water and 2.5 ml of a solution of the polymer product of Part B in screw cap tubes. The tubes were gassed for a few minutes with $N_2$, sealed and incubated for 48 hours at 35° C. Samples were removed from the tubes periodically by hypodermic needle and syringe in order to measure azo reduction by decrease in visible absorbance at the $\lambda_{max}$. It was observed that in the absence of the redox mediator dye benzylviologen, the polymeric compound is azo-bond reduced about 50% in 6 hours. In the presence of benzylviologen the polymers' azo bonds are completely reduced by the bacteria in less than two hours.

These findings are consistent with those obtained with a number of polymeric azo dyes studied previously. These studies [Brown, J. P., "Reduction of polymeric azo dyes by cell suspensions of enteric bacteria," *Abstr. An. Meet. Amer. Soc. Microbiol.*, p. 123 (1976); Brown, J. P.; Wilcox, A. S.; and MacMillan, J. M.; "The redox shuttle: A novel mechanism for the extra cellular reduction of azo and nitro xenobiotics by intestinal bacteria." *Abstr. XII Inter. Cong. Microbiol.*, Munich, p. 117 (1978)] are compared with the present results in Table 1. It may be suggested that there is participation of low molecular weight metabolites in the extracellular reduction of azo polymers by intestinal bacteria. This indicates a degradation mechanism which would act on aromatic azo bonds irrespective of the structure of the polymer in which they are incorporated.

The method of Hansson was used with modifications for the extraction and quantitation of 5-ASA in the biological specimens.

One milliliter of 0.1 M phosphate buffer pH 6.9 was added to approximately 1 gram of the sample followed by 110 units of β-glucuronidase. The samples were incubated overnight at 37° C. in 15 ml extraction tubes. Acetic anhydride (25 μl) was added to each extraction tube, and mixed. One milliliter of 1 M HCl was then added and mixed and followed by 5 ml of 4-methyl-2-pentanone. Extraction was accomplished on a mechanical shaker for 20 minutes at 240 cycles per minute. Centrifugation separated the organic layer from the aqueous material. Four milliliters of the pentanone were removed and extracted with 3 ml of 0.5 M phosphate buffer pH 6.0. After centrifugation, the organic layer was discarded, and the aqueous portion was assayed for fluorescence in an Aminco-Bowman spectrofluorimeter (Model No. SPF-125). An (uncorrected) excitation wavelength of 295 nm was used and fluorescence at 460 nm (uncorrected) was measured. Standards were treated the same as the samples and were run in parallel with each set of biological specimens. This procedure allowed detection of the three major metabolites of SASP and Poly ASA-171: the flucuronic acid conjugate of 5-ASA, the N-acetylated metabolite of 5-ASA, and the unmetabolized 5-ASA.

In the first experiment with four rats, standard curves were constructed using 5-ASA. In the second experiment with six rats, the N-acetyl derivative of 5-ASA was found to give better linearity from 0.5 to 500 nmol per gram of specimen. Calculations of 5-ASA content were based on the appropriate standard curve for each particular extraction.

Experiment I revealed large individual variations in

TABLE 1

Comparison of Polymeric 5-ASA and Polymeric Dye Reduction by Anaerobic Cell Suspension of Rat Cecal Bacteria Polymeric Azo Substrates and Quantities per Tube

| (h) time | Polymeric 5-ASA | | | | Polymeric Azo Dye | | | |
|---|---|---|---|---|---|---|---|---|
| | 1.4μ equiv. + | | 14μ equiv. | | 1.5μ equiv. | | 15μ equiv. | |
| | −BZV | +BZV | −BZV | +BZV | −BZV | +BZV | −BZV | +BZV |
| 0 | 3.56 | 3.56 | 21.36 | 21.36 | 2.63 | 2.63 | 15.78 | 15.78 |
| 2 | 2.50 | 0 | 7.4* | 7.4* | 2.48 | 0 | 4.92* | 4.56* |
| 4 | 2.10 | NM | 7.8* | 8.1* | 2.32 | NM | 5.16* | 4.35* |
| 6 | 1.82 | NM | 7.5* | 7.4* | 2.12 | NM | 4.98* | 3.90* |
| 24 | *** | NM | *** | *** | * | NM | * | * |

Notes:
+1.0μ equivalent of azo bond/3.05 ml ∼ 0.33 mM.
√A$_{\lambda\,max}$ of supernatant after sedimentation of bacteria.
*Dye observed to bind to bacteria.
***Excessive binding of dye to bacteria.
NM Not measured.

The applicability of in vitro studies of azo bond reduction to simulate in vivo reduction has also been demonstrated by studies of the intestinal absorption of reduction products of orally-administered azo dyes (Honohan, T., et al., "Intestinal absorption of polymeric derivatives of the food dyes sunset yellow and tartrazine in rats," *Xenobiotica*, 7:765 (1977)).

The polymer of Part B was fed to acclimated female Simonsen rats (200–300 g). Nonfasted rats were dosed with 20 mg of the polymer (ca. 40 μmole of 5-ASA as an aqueous solution). For purposes of comparison, a control group was dosed with ca. 40 μmole of potential 5-ASA in the form of an aqueous suspension of SASP. Blood, urine and fecal specimens were collected at regular intervals from both groups.

urinary and fecal excretion kinetics and serum concentrations of 5-ASA. Rat number 1 consistently showed low recovery values of 5-ASA in urine and feces compared with the other three rats and was considered abnormal with regard to absolute quantities of 5-ASA recovered during the course of the experiment. However, the qualitative comparisons between rat number 1 and the other animals do show consistent trends.

These trends are: (a) a major percentage of the total urinary excretion of 5-ASA (87 to 97%) is excreted between 12 and 48 hours; (b) a major percentage of the total fecal excretion of 5-ASA (81 to 93%) is excreted between 4 and 48 hours; (c) peak serum concentration occurs at 12 hours (in 3 out of 4 rats).

The total percent recovery of 5-ASA in three out of four animals was calculated to be greater than 100% (Table 2). These recovery values are artifacts of the standard material (5-ASA) and extrapolation of fluorescence values of the experimental samples beyond the limits of the standard curve. Thus, these values are erroneously high in a quantitative sense, but can still be used as relative comparisons in a qualitative sense.

TABLE 2

Percent of dose received as 5-ASA and metabolites in biological samples (Experiment I)

| Test Agent | Rat # | Urine | Feces | Total | % Recovery |
|---|---|---|---|---|---|
| SASP | 1 | 2.7 | 4.7 | 7.4 | 18.0 |
|  | 2 | 33.2 | 13.6 | 46.8 | 117.0 |
| Polymeric 5-ASA | 3 | 28.6 | 17.2 | 45.8 | 122.0 |
|  | 4 | 35.2 | 7.3 | 42.5 | 114.0 |

Experiment II utilized the N-acetyl derivative of 5-ASA as a standard and gave much better linearity of fluorescence (from 0.5 to 500 nmol). All fluorescence values of experimental samples fell within the range of the standard curves and are considered to be more accurate determinations of 5-ASA content. This second study also used shorter time intervals of fecal and urinary collection in order to more accurately assess the excretion kinetics (Table 3).

The large individual variations discovered in the first study persisted in the second study, but the trends remained very similar: (a) a major percentage of the total urinary excretion of 5-ASA (39 to 83%) is excreted between 12 and 24 hours; (b) a major percentage of the total fecal excretion of 5-ASA (69 to 98%) is excreted between 8 and 36 hours; (c) peak serum concentration remained at the 12-hour time point.

Since this second study included three animals within each group, a statistical analysis of the results of the second study was completed to assess any quantitative trends (Tables 4 and 5). The 5-ASA recovery of the urine was significantly higher in the polymer-fed group (8.0 vs. 3.7). However, 5-ASA recovery in the feces and total recovery of 5-ASA are not significantly different. The peak serum 5-ASA concentration of the pplymer group was lower (2.5 vs. 5.6), but not significantly lower than the SASP group.

The results of these experiments showed that SASP and the polymer product had similar patterns of 5-ASA cleavage product delivery to the lower bowel contents, blood serum and urine. No SP delivery was observed with the polymer. Hence, it is considered that the polymer product would exhibit efficacy in the treatment of ulcerative colitis and decrease the incidence of side effects known with conventional monomeric equivalents.

TABLE 3

Percent recovery of 5-ASA in urine samples at various time intervals (Experiment II)[a]

| Rat # | Time Interval | % Recovery | Cumulative % |
|---|---|---|---|
| SASP group 1 | 0–4 | 4.98 | 4.98 |
|  | 4–12 | 13.88 | 18.86 |
|  | 12–24 | 42.11 | 60.97 |
|  | 24–36 | 14.91 | 75.88 |
|  | 36–48 | 20.18 | 96.06 |
|  | 48–72 | 2.52 | 98.58 |
|  | 72–96 | 1.41 | 99.99 |
| 2 | 0–4 | 3.29 | 3.29 |
|  | 4–12 | 0.75 | 4.04 |
|  | 12–24 | 77.60 | 81.64 |
|  | 24–36 | 11.78 | 93.42 |
|  | 36–48 | 6.58 | 100.00 |
|  | 48–72 | 0.00 | 100.00 |
|  | 72–96 | 0.00 | 100.00 |
| 3 | 0–4 | 0.00 | 0.00 |
|  | 4–12 | b | 0.00 |
|  | 12–24 | 83.44 | 83.44 |
|  | 24–36 | 6.58 | 90.02 |
|  | 36–48 | 6.99 | 97.01 |
|  | 48–72 | 2.98 | 99.99 |
|  | 72–96 | 0.00 | 99.99 |
| Polymeric 5-ASA group 4 | 0–4 | 0.00 | 0.00 |
|  | 4–12 | 16.51 | 16.51 |
|  | 12–24 | 52.50 | 69.01 |
|  | 24–36 | 20.51 | 89.52 |
|  | 36–48 | 7.03 | 96.55 |
|  | 48–72 | 2.76 | 99.31 |
|  | 72–96 | 0.68 | 99.99 |
| 5 | 0–4 | 0.24 | 0.24 |
|  | 4–12 | 24.64 | 24.88 |
|  | 12–24 | 67.33 | 92.21 |
|  | 24–36 | 6.48 | 98.69 |
|  | 36–48 | 1.30 | 99.99 |
|  | 48–72 | 0.00 | 99.99 |
|  | 72–96 | 0.00 | 99.99 |
| 6 | 0–4 | 0.00 | 0.00 |
|  | 4–12 | 38.52 | 38.52 |
|  | 12–24 | 38.86 | 77.36 |
|  | 24–36 | 20.57 | 97.95 |
|  | 36–48 | 2.05 | 100.00 |
|  | 48–72 | 0.00 | 100.00 |
|  | 72–96 | 0.00 | 100.00 |

[a]Values are based on total cumulative urinary excretion of 5-ASA and its metabolites at the end of 96 hours.
[b]Sample was destroyed during the extraction procedure.

TABLE 4

Percent of dose recovered as 5-ASA and its metabolites in biological samples[a] (Experiment II)

| Test Agent | Rat # | Urine | Feces | Total |
|---|---|---|---|---|
| SASP | 1 | 3.0 | 7.7 | 10.7 |
|  | 2 | 3.2 | 14.0 | 17.2 |
|  | 3 | 5.0 | 11.4 | 16.4 |
|  | X̄ ± SD | 3.7 ± 1.1 | 11.0 ± 3.2 | 14.7 ± 3.4 |
| Polymeric 5-ASA | 4 | 6.7 | 5.3 | 12.0 |
|  | 5 | 9.5 | 9.4 | 18.9 |
|  | 6 | 7.7 | 22.0 | 29.7 |
|  | X̄ ± SD | 8.0 ± 1.4[b] | 12.3 ± 8.7 | 20.2 ± 8.9 |

[a]Based on 40 μmole of 5ASA in the oral dose.
[b]Significantly different from the SASP group at the $P \leq 0.05$ level Students' t test.

TABLE 5

Peak serum concentration of 5-ASA and its metabolites (Experiment II)[a]

| Test Agent | Rat # | Peak Serum Concentration (nmol. 5-ASA/ml) |
|---|---|---|
| SASP | 1 | 7.9 |
|  | 2 | 4.0 |
|  | 3 | 4.8 |
|  | X̄ ± SD | 5.6 ± 2.1 |
| Polymeric 5-ASA | 4 | 1.8 |
|  | 5 | 2.6 |
|  | 6 | 3.0 |
|  | X̄ ± SD | 2.5 ± 0.6[a] |

[a]Difference in means not statistically significant at the $P \leq 0.05$ level. Students' t test.

D. Compounding of Pharmaceutical Preparations

The product of Part B is formed into a variety of pharmaceutical dosage forms as follows:

| Tablets: | |
|---|---|
| Three tablet formulations, T-1, T-2, and T-3 are compounded with the following materials: | |
| Formulation T-1 | |
| Polymeric 5-ASA as prepared in Part B | 6 g |
| Lactose (diluent) | 3 g |
| 10% Starch Paste (binder) | 1 g |
| Formulation T-2 | |
| Polymeric 5-ASA as prepared in Part B | 8 g |
| Carboxymethylcellulose (disintegrator) | 2 g |
| Formulation T-3 | |
| Polymeric 5-ASA as prepared in Part B | 10.0 g |
| 20% gelatin solution | 0.5 g |
| Sodium chloride (lubricant) | 0.5 g |
| FD&C Red 40 lake | 0.005 g |

Each of these formulations is thoroughly mixed using granulation techniques and then formed into compressed tablets of 100 and 250 mg size.

Capsules:

Product of Part B is ground with an equal part by weight of mannitol. The resulting admixture powder is hand-filled into number 1 gelatin capsules.

Suppositories:

A fine powder of the product of Part B (5 g) is admixed with 30 g of liquid theobroma oil at 40° C.; the resulting suspension is poured into a chilled rectal suppository mold to form 10 suppositories each containing 0.5 g of medicament.

Other Forms:

The product of Part B could be compounded into solutions and suspensions with pharmacologically acceptable solvents and suspending aids.

Administration of these dosage forms to man and other mammals is effected by art-accepted techniques. In such administration, delivery of a therapeutically effective dose of 5-aminosalicylic acid is effected.

EXAMPLE II

A polymer based on Poly(N-methylvinylamine) capable of releasing 5-aminosalicylic acid in the intesting is prepared as follows:

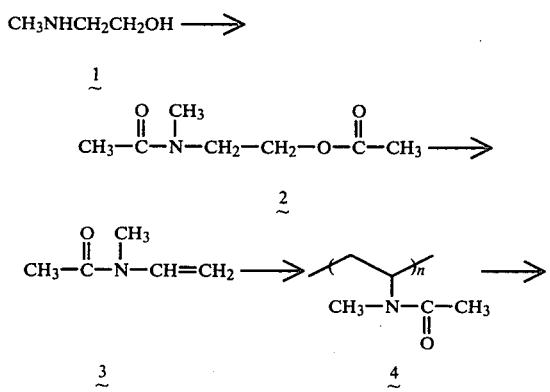

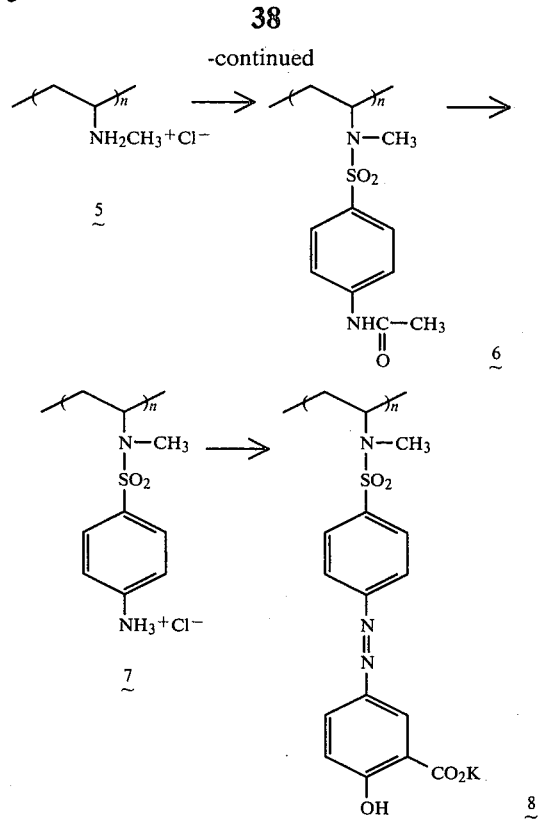

A. Preparation of 2

N-Methylaminoethanol (250 g, 3.33 mol) is added dropwise over 60 minutes to acetic anhydride (691 g, 6.77 mol) maintained at 115°–120° C. The product is isolated by vacuum distillation (bp 95°–98° C./0.1 mm) in 93% yield as a colorless oil.

B. N-Methyl-N-vinylacetamide (3)

The product of step A is pyrolyzed by passing 642 g (4.04 mol) at a rate of 1.17 g/min through a Pyrex helicespacked quartz tube (3.5 cm diameter, 40 cm length) maintained at 480° C. A 400 ml/minute argon flow is employed. The crude pyrolyzate (629 g of dark orange oil) is distilled to afford 119 g (1.20 mol, 29.8% yield) of 3 (bp 72° C./20 mm).

C. Poly(N-methyl-N-vinylacetamide) (4)

A 2-liter, 3-neck flask, equipped with overhead stirrer, reflux condenser topped with an Argon inlet, and internal thermometer, is charged with 99.0 g (1.00 mol) of distilled N-methyl-N-vinylacetamide, 3.28 g (0.02 mol) of AIBN, and 900 ml of thoroughly degassed $H_2O$. The flask is thoroughly purged with argon and held in a bath maintained at 65° C. for 24 hours. A TLC ($SiO_2$, ethyl acetate) shows no monomer ($R_f$ 0.47) remaining.

A 4.0-ml sample is removed for analysis, while the bulk is directly employed in part D. The sample is determined by gel permeation chromatography techniques to possess a molecular weight of $1.6 \times 10^5$. Anal. Calcd for $(C_5H_9NO)_n$: C, 60.54; H, 9.15; N, 14.12. Found: C, 59.96; H, 9.49; N, 13.95.

D. Poly(N-methylvinylamine) hydrochloride (5)

The reaction mixture from part C is treated with 208 ml (2.50 mol) of 12 N HCl, placed in a teflon-lined, stirred autoclave, and heated at 125° C. for 72 hours. The crude product is cooled, evaporated to a volume of approximately 300 ml, and precipitated into 15 liters of well-stirred iso-propyl alcohol. The product is filtered, washed with 2 liters of iso-propyl alcohol, and dried (50° C./0.1 mm/48 hours). The yield is 86.2 g of granular solid possessing a nitrogen content of 10.43 mequiv/g by elemental analysis. Titration provides an amine value of 10.5 mequiv/g, indicating that hydrolysis is complete. The yield for polymerization/hydrolysis, based on nitrogen recovery, is 90.0%.

E. Schotten-Baumann Reaction

A 1000-ml, 3-neck flask, equipped with overhead stirrer, pH probe, and 125-ml dropping funnel filled with 8 N NaOH, is charged with 21.1 g (220 mequiv of amine) of 5 and 300 ml of $H_2O$. The flask is flushed with argon and stirred until solution is complete. The solution is then treated with 22.5 ml (180 mmol) of 8 N NaOH (pH 10.0) and 150 ml of 2-methoxyethanol.

The N-acetylsulfanilyl chloride (64.5 g, 276 mmol) is then added in three equal portions of 21.5 g. The second and third additions are accompanied by 150 ml of 2-methoxyethanol.

The second addition takes place 5 minutes after the first, with the third addition taking place 15 minutes after the second. During the reaction period the pH is maintained at 9-10 by the addition of 8 N NaOH as necessary. After the final sulfonyl chloride addition, the pH is maintained at 9-10 for 30 minutes, and then raised to 10.5-11.0 and held for 1.5 hours. At the end of the reaction the pH is stable. The amount of 8 N NaOH employed during the Schotten-Baumann reaction is 47.0 ml (376 mmol).

The reaction mixture is added dropwise to 18 liters of well-stirred $H_2O$ and 6 is isolated by filtration, washed thoroughly with $H_2O$, and dried (50°/0.1 mm/48 hours). The yield is 50.5 g (94.4% of theory). Elemental analysis provides a sulfur content of 3.78 mequiv/g and an N/S ratio (mequiv/g basis) of 2.06 (2.00 in theory).

F. Preparation of Polysulfanilamide 7

A 2-liter, 3-neck flask, equipped with oil bath, overhead stirrer, and reflux condenser, is charged with 50.5 g of 6 (191 mequiv of sulfur), 846 ml of $H_2O$, and 95.5 ml (114 g, 1.15 mol) of 12 N HCl. The initial polymer concentration in this mixture is 5.0 wt %.

With overhead stirring, the bath temperature is raised to 125° C. (gentle reflux) and held for 18 hours. The solution of 7 is allowed to cool to room temperature, passed through a coarse-frit funnel, and directly employed in step G.

G. Diazotization and Coupling

The solution from step F (964 g total weight) is placed in a 3-liter, 3-neck flask equipped with an overhead stirrer. The polymer solution is diluted with 1500 ml of $H_2O$ to provide an overall polymer concentration of approximately 2 wt %. 19.5 g (229 mmol) of $KNO_2$ is dissolved in 8.0 ml of $H_2O$ by briefly stirring. The solution of 7 is stirred at a moderate rate as the $KNO_2$ is added in one portion at room temperature. The perfectly clear polymeric diazonium salt solution that is produced is immediately immersed in an ice bath and stirred. A positive KI-starch test is obtained.

A plastic bucket (capacity ~10 liters), fitted with overhead stirrer, thermometer, pH probe, and 250 ml dropping funnel filled with 8 N KOH, is charged with 79.0 g (573 mmol) of salicylic acid, 3000 ml of $H_2O$, and 143 ml (1146 mmol) of 8 N KOH. The mixture is stirred until solution is complete (<5 minutes).

The potassium salicylate solution (pH 13.35) is cooled to 15° C. by the addition of a small amount of ice and the diazonium salt solution (held in the ice bath) is added at a steady rate via peristaltic pump over 20 minutes. During the coupling the pH is maintained at 13.1-13.3 by the dropwise addition of 8 N KOH (170 ml, 1360 mmol). The final volume of the coupling solution is 7.0 liters, and the temperature rises to 17° C.

The dark-brown solution is diluted to 18 liters with $H_2O$, passed through a coarse-frit filter, concentrated by ultrafiltraiton with a model HIP10 cartridge (molecular weight 10,000 cutoff, Amicon Corp., Lexington, Mass.), and then ultrafiltered for 6×4-liter diavolumes with the same cartridge.

The solution is concentrated to a volume of 500 ml and freeze dried to provide about 66.9 g (87.8% of theory) of 8 which is capable of undergoing azo bond cleavage in the colon, as described in Example I. A small sample is dried (50° C./0.1 mm/8 hours) and submitted for elemental analysis. The N/S ratio (mequiv/g basis) is 3.00 (3.00 in theory).

EXAMPLE III

A polymer based on poly(N-vinylamine-co-sodium acrylate) capable of releasing 5-aminosalicylic acid in the colon is prepared as follows.

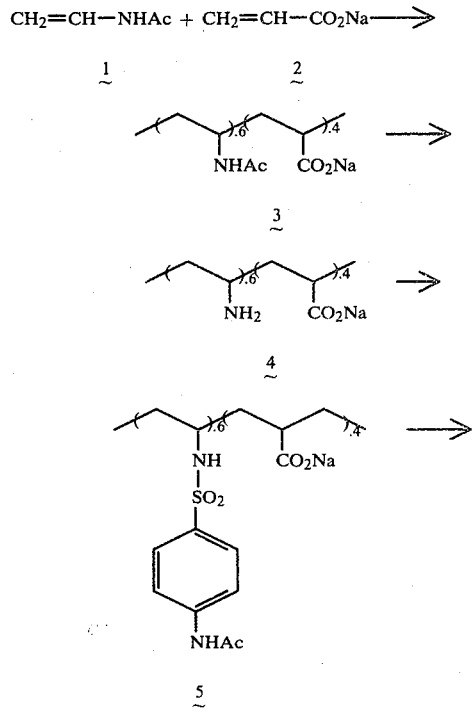

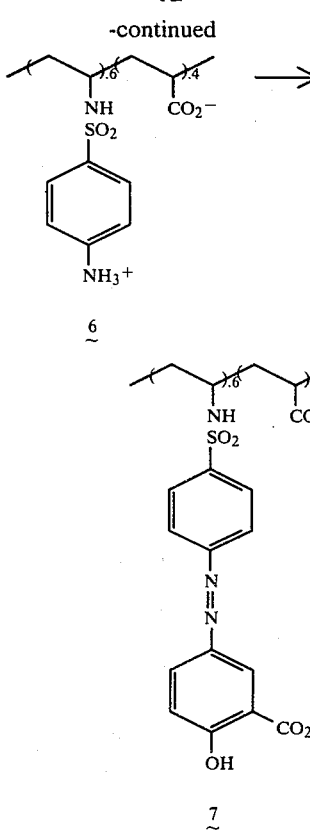

The vinylacetamide (1) employed in this example, is prepared by the pyrolysis of ethylidene bisacetamide, as set forth in *J. Chem. Soc.*, 98, 5996 (1976).

A. Purification of N-vinylacetamide

A 3144 g (3000 ml) sample of aqueous 1, containing 743 g (8.74 mol) of this monomer by GC assay, is diluted with 3000 ml of distilled H$_2$O and divided into three equal portions. Each 2000-ml portion is extracted with ether (9×1000 ml). The extracts are combined, and 3000-ml portions thereof are washed with H$_2$O (100 ml), brine (250 ml), and dried (Na$_2$SO$_4$ and then MgSO$_4$). The dried portions are combined and the solvent removed by rotary evaporation. Benzene is employed to azeotrope traces of residual H$_2$O. After final drying (25° C., 0.1 mm, 8 hours), there is obtained 477 g (5.62 mol, 64.3% recovery) of 1 as a white solid.

Each of the 2000-ml aqueous portions are saturated with NaCl (400 g each) and extracted with ether (3×1000 ml). The ethereal extracts are treated as before to provide an additional 137 g (1.61 mol, 18.4% recovery) of 1. Total recovery is 614 g (7.22 mol, 82.6%).

B. Poly(N-vinylacetamide-co-sodium acrylate) (3)

A 2-liter, four-neck flask, equipped with overhead stirrer, thermometer, reflux condenser, and argon inlet, is charged with 104 g (1.22 mol) of 1, 59.0 g (0.82 mol) of acrylic acid, 103 ml (0.82 mol) of 8 N NaOH, 5.0 g (0.03 mol) of AIBN, and 400 ml of H$_2$O. The mixture is thoroughly deoxygenated and heated at 65° C. (internal) for 18 hours. After cooling, the solution is filtered, evaporated, and precipitated by slow addition to 14 liters of rapidly stirred acetone. Copolymer 3 is isolated by filtration, washed with acetone, and dried (50° C./0.1 mm/24 hours). The yield is 176.5 g (97.5% of theory). The product is determined by gel permeation chromatography techniques to possess a molecular weight of 8.6×10$^4$. Anal. Calcd for (C$_4$H$_7$NO)$_{0.6}$ (C$_3$H$_3$O$_2$Na)$_{0.4}$: C, 48.76; H, 6.09; N, 9.48. Found: C, 48.55; H, 6.93; N, 10.31.

C. Poly (N-vinylamine-co-sodium acrylate) (4)

A 1-liter, three-neck flask, equipped with overhead stirrer and reflux condenser, is charged with 150 g (1.10 mol amide) of 3, 300 ml of H$_2$O, and 250 ml (3.00 mol) of 12 N HCl. The solution is refluxed for 72 hours, cooled, and precipitated 4 isolated by decantation. The copolymer is dissolved in 250 ml of 2 N NaOH, and reprecipitated by slow addition to 14 liters of rapidly stirred methanol containing 250 ml of 12 N HCl. The precipitate is filtered, washed with methanol, and dried (50° C./0.1 mm/24 hours) to afford 113.2 g of 4 as a white solid. Elemental analysis shows the C/N ratio (mequiv/g basis) to be 4.02 (4.00 in theory). Proton titration and $^{13}$C NMR show the hydrolysis to be complete.

D. Schotten-Baumann Reaction

A 1000-ml, 3-neck flask, equipped with overhead stirrer, pH probe, and 125-ml dropping funnel filled with 8 N NaOH, is charged with 25.0 g (0.232 mol of amine) of copolymer 4 (9.26 mequiv N/g by elemental analysis), 300 ml of H$_2$O, 300 ml of 2-methoxyethanol, and 25 ml (0.20 mol) of 8 N NaOH. The flask is flushed with argon and stirred until solution is complete.

The N-acetylsulfanilyl chloride (81.3 g, 0.348 mol) is then added in three equal portions of 27.1 g over a period of 1.5 hours. During the reaction the pH is maintained at 10–11 by the addition of 8 N NaOH (49.3 ml, 0.394 mol employed). The pH becomes stable 1.0 hour after the final addition of sulfonyl chloride.

The reaction mixture is evaporated to approximately half volume, and added dropwise to 18 liters of well-stirred methanol. Precipitated 5 is isolated by filtration, washed thoroughly with methanol, and dried (50° C./0.1 min/72 hours). The yield is 60.3 g (85.9% of theory). Elemental analysis provides a sulfur content of 3.34 mequiv/g and an N/S ratio (mequiv/g basis) of 2.01 (2.00 in theory). Anal. Calcd for (C$_{10}$H$_{12}$N$_2$O$_3$S)$_{0.6}$ (C$_3$H$_3$O$_2$Na)$_{0.4}$:C, 48.43; H, 4.71; N, 9.42; 5, 10.76. Found: C, 47.92; H, 4.91; N, 9.41; S, 10.71.

E. Preparation of Polysulfanilamide 6

A 2-liter, 3-neck flask, equipped with oil bath, overhead stirrer, and reflux condenser, is charged with 60.3 g of 5 (201 mequiv of sulfur), 1030 ml of H$_2$O, and 101 ml (120 g, 1.21 mol) of 12 N HCl. The initial polymer concentration in this mixture is 5.0 wt %.

With overhead stirring, the bath temperature is raised to 125° C. (gentle reflux) and held for 18 hours. The solution of 6 is allowed to cool to room temperature, passed through a coarse-frit funnel, and directly employed in the following step.

F. Diazotization and Coupling

The solution from step E (1194 g total weight) is placed in a 3-liter, 3-neck flask equipped with an overhead stirrer, and diluted with 1200 ml of H$_2$O to provide an overall polymer concentration of approximately 2.5 wt %. The solution is stirred at a moderate rate as 48.2 ml (0.241 mol) of 5 N NaNO$_2$ is added in one portion at room temperature. The clear polymeric diazonium salt solution that is produced is immediately immersed in an ice-bath and stirred. A positive KI-starch test is obtained.

A plastic bucket (capacity approximately 10 liters), fitted with overhead stirrer, thermometer, pH probe, and 250-ml dropping funnel filled with 8 N NaOH, is charged with 55.5 g (0.402 mol) of salicylic acid, 2000 ml of H₂O, and 101 ml (0.808 mol) of 8 N NaOH. The mixture is stirred until solution is complete (<5 minutes).

The sodium salicylate solution (pH 13.25) is cooled to 14° C. by the addition of ice, and the diazonium salt solution (held in the ice bath) is added at a steady rate via peristaltic pump over 15 minutes. Throughout the coupling the pH is maintained at 13.1–13.3 by the dropwise addition of 8N NaOH (179 ml, 1.43 mol). The final volume of the coupling solution is 5.5 liters, and the temperature rises to 21° C.

The dark-brown solution is diluted to 18 liters with H₂O, passed through a coarse-frit filter, concentrated by ultrafiltration with an H1P10 cartridge, and then ultrafiltered for 6×4-liter diavolumes with the same cartridge.

The solution is concentrated to 750 ml and freeze dried to provide 79.9 g (92.1% of theory) of copolymeric drug 7. A small sample is dried (50° C./0.1 mm/8 hours) and submitted for elemental analysis. This provides a sulfur content of 2.24 mequiv/g, and an N/S ratio (mequiv/g basis) of 3.03 (3.00 in theory). Anal.. Calcd for $(C_{15}H_{12}N_3O_5SNa)_{0.6}$ $(C_3H_3O_2Na)_{0.4}$:C, 47.26; H, 3.24; N, 9.73; S, 7.41. Found: C, 46.85; H, 3.67; N, 9.52; S, 7.18.

This material is capable of undergoing cleavage in the colon and releasing.

EXAMPLE V

A polymer based on poly(ethylenimine) capable of yielding 5-aminosalicylic acid in the intestine is prepared as follows. The drug produced, because of the overall amphoteric nature of the polymer (anionic salicylate carboxyl groups and cationic backbone tertiary amine groups), is essentially insoluble below pH 10.

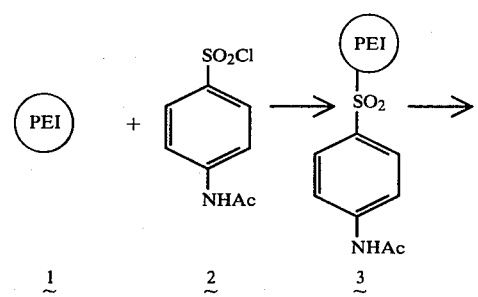

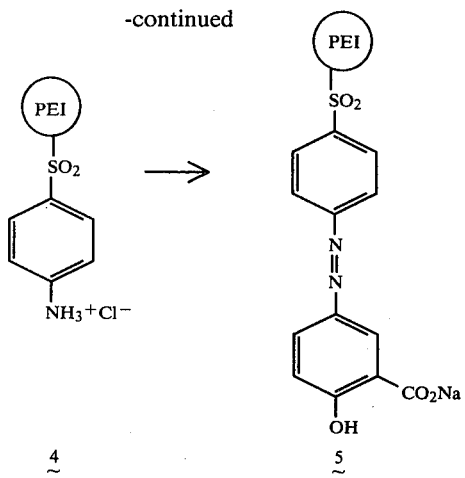

The poly(ethylenimine) used in this example is obtained from Polysciences, Inc., Warrington, Pennsylvania (lot #2632). The sample is labeled as a 33 wt % aqueous solution of molecular weight $4.0$–$6.0 \times 10^4$ polymer. Elemental analysis of the solution provides a value of 8.07 mequiv N/g, and titration of the solution shows 5.29 mequiv titratable amine/g.

A. Schotten-Baumann Reaction

A 1000-ml, 3-neck flask, equipped with overhead stirrer, pH probe, and 125-ml dropping funnel filled with 8 N NaOH, is charged with 23.4 g of poly(ethylenimine) solution, 300 ml of H₂O, and 150 ml of THF. Stirring is begun under argon. The solution is clear and possesses a pH of 10.

The solution is treated with 18.4 g (78.7 mmol) of N-acetylsulfanilyl chloride (2), stirred for 5 minutes, and the pH maintained at 9–10 by the addition of 8 N NaOH (12 ml, 96 mmol). The solution is then treated with a second equal portion of sulfonyl chloride 2 and 150 ml of THF while maintaining the pH at 9–10 by the addition of 8 N NaOH (12 ml, 96 mmol) over 15 minutes.

The mixture, now an emulsion, is treated with a third equal portion of 2 and 150 ml of THF. The pH is maintained at 10–11 by the addition of 8 N NaOH (15 ml, 120 mmol) over 60 minutes.

The emulsion is transferred to a 2-liter, one-neck flask is subjected to rotary evaporation. After all the THF is evaporated, polymer 3 is obtained as a granular off-white solid. The product is broken up, filtered, washed well with H₂O, and dried (50° C./0.1 mm/5 hours). The yield is 37.0 g, and elemental analysis (C, 50.85; H, 5.72; N, 12.04; S, 12.09) provides a sulfur content of 3.77 mequiv/g.

B. Hydrolysis

A 500-ml, 3-neck flask, equipped with overhead stirrer, oil bath, and reflux condenser, is charged with 5.00 g of 3 as prepared above (18.9 mequiv of sulfur), 9.43 ml (113 mmol) of 12 N HCl, and 234 ml of H₂O. With stirring, the mixture is refluxed for 10 hours, cooled, filtered (coarse-frit funnel), and directly employed in step C.

C. Diazotization and Coupling

The solution of 4 is placed in a 500-ml, 3-neck flask equipped with an overhead stirrer. The solution is stirred at a moderate rate as 4.70 ml (23.5 mmol) of 5 N NaNO$_2$ is added in one portion at room temperature. The clear solution is cooled in an ice bath as stirring is continued. A positive KI-starch test is obtained.

A 2-liter beaker, fitted with overhead stirrer, thermometer, pH probe, and 50-ml dropping funnel filled with 8 N NaOH, is charged with 6.49 g (47.0 mmol) of salicylic acid, 500 ml of H$_2$O, and 12.5 ml (100 mmol) of 8 N NaOH. The mixture is stirred until solution is complete (<5 minutes).

The sodium salicylate solution (pH 13.6) is cooled to 12° C. by the addition of ice, and the diazonium salt solution is added dropwise over 25 minutes via a 250-ml dropping funnel. The pH is maintained at 13.3–13.6 throughout the coupling by the addition of 8 N NaOH (22.0 ml, 176 mmol).

The solution of crude $\underline{5}$ is evaporated to a volume of approximately 250 ml of neutralized to pH 7.5 by the dropwise addition of 1.0 N HCl with vigorous stirring. The precipitated product is isolated by centrifugation (crude yield 7.01 g). The crude product is purified by redissolution in 0.1 N NaOH (150 ml), and precipitation into methanol. The yield, after thorough drying (50° C./0.1 mm/48 hours), is 6.57 g. Elemental analysis gives a sulfur content of 2.68 mequiv/g.

EXAMPLE V

A polymer based on polystyrene capable of yielding 5-aminosalicylic acid in the colon is prepared as follows.

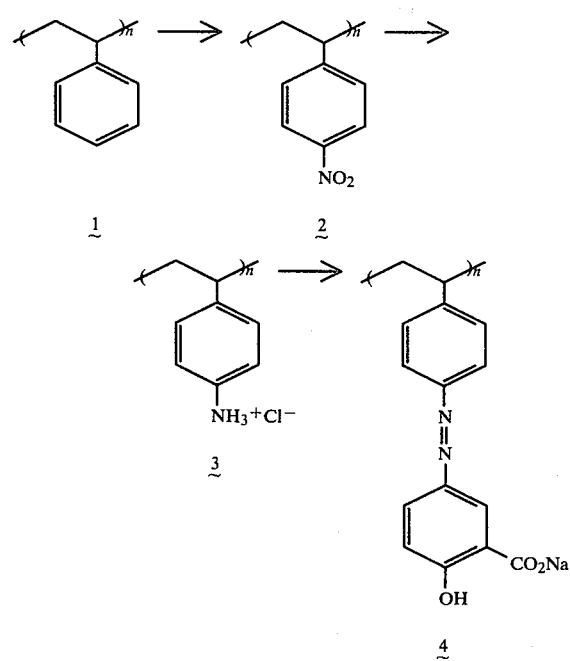

A. Preparation of 100% Nitric Acid

Pure HNO$_3$ is prepared following the procedure of P. Liang, "Organic Syntheses," Coll. Vol. III, E. C. Horning, Ed., John Wiley and Sons, New York, NY, 1955, pp 803–5. A 500-ml, one-neck flask is charged with 150 ml of 96% H$_2$SO$_4$ and 150 ml of 90% HNO$_3$ (J. T. Baker cat. no. 9624), and rigged for distillation under argon. There is obtained 131.5 g (2.09 mol) of HNO$_3$ (bp 79°–81° C.) as a light yellow liquid. The acid is stored in the freezer prior to step B.

B. Nitration of Styrene

A 250-ml, 3-neck flask, equipped with overhead stirrer, low-temperature thermometer, argon inlet, and cooling bath, is charged with 131.5 g (2.09 mol) of HNO$_3$ and cooled to an internal temperature of −30° C. Finely powdered polystyrene (21.0 g, 0.202 mol, molecular weight determined to be 1.3×10$^5$ by gel permeation chromatography techniques) from Cellomer Associates (Webster, NY) is added portionwise over 2 hours while maintaining the temperature at −30° C. After stirring for an additional hour at this temperature, the viscous mass is allowed to slowly warm to ambient temperature and stir for 24 hours.

Crude $\underline{2}$ is isolated by direct precipitation of the reaction mixture into 3 liters of ice water. The product is filtered, washed with H$_2$O, and thoroughly ground in a commercial blender with H$_2$O. The product is again filtered, washed with H$_2$O and then acetone, and dried (50°/0.1 mm/24 hours). The yield of off-white solid is 33.1 g (110% of theory): Anal. Calcd for (C$_8$H$_7$NO$_2$)$_n$: C, 64.43; H, 4.70; N, 9.39. Found: C, 63.72; H, 4.49; N, 9.83.

C. Preparation of p-Aminopolystyrene ($\underline{3}$)

A 100-ml, 2-neck flask, equipped with overhead stirrer and argon inlet, and rigged for distillation, is charged with 2.00 g (13.4 mmol) of $\underline{2}$ and 50 ml of 97% phenylhydrazine (Aldrich Chemical Co., Milwaukee, Wis). With vigorous stirring, the mixture is heated to 200° C. (bath) and there maintained for 3 hours. During this period the polymer dissolves, and approximately 5 ml of low boiling liquid is removed by distillation.

The reaction mixture is cooled to room temperature and directly precipitated into 2 liters of diethyl ether. The p-aminopolystyrene obtained is filtered and immediately dissolved in 500 ml of 0.5 N HCl. This solution is evaporated and the product dried (25° C./0.1 mm/18 hours) to give 2.00 g (12.9 mmol, 96.2% yield) of p-aminopolystyrene hydrochloride ($\underline{3}$). Anal. Calcd for (C$_8$H$_{10}$NCl)$_n$: C, 61.74, H, 6.43; N, 9.00; Cl, 22.83. Found: C, 62.00; H, 6.61; N, 8.81; Cl, 22.56.

D. Diazotization and Coupling

A 5-liter, 3-neck flask, equipped with overhead stirrer and cooling bath, is charged with 75.0 g (0.482 mol) of $\underline{3}$, 101 ml (120 g, 1.21 mol) of 12 N HCl, and 3555 ml of H$_2$O. The mixture is stirred until solution is complete, cooled to 10° C. (internal), and treated (rapidly in one portion) with 116 ml (0.580 mol) of 5 N NaNO$_2$. The perfectly clear polymeric diazonium salt solution that is produced is immediately cooled to 0° C. with continued stirring. A positive KI-starch is obtained.

A 25-liter battery jar, equipped with overhead stirrer, thermometer, pH probe, and 500-ml dropping funnel filled with 8 N NaOH is charged with 99.8 g (0.723 mol) of salicyclic acid, 5000 ml of H$_2$O, and 188 ml (1.50 mol) of 8 N NaOH. The mixture is stirred until solution is complete (pH 13.40), and cooled to 8° C. by the addition of ice.

The polymeric diazonium salt solution (maintained at 0° C.) is added to the salicylate solution by peristaltic pump over 30 minutes. During this period, the pH is maintained at 13.0–13.5 by the addition of 8 N NaOH (123 ml, 0.982 mol) and the temperature is controlled at 15°–20° C. by the addition of ice.

The solution (approximately 15 liters in volume) is passed through a coarse-frit filter, concentrated by ultrafiltration with an H1P10 cartridge, and ultrafiltered for 6×10-liter diavolumes with the same cartridge.

The solution is concentrated to 3000 ml and freeze dried to provide 121.7 g (0.420 mol, 87.1% yield) of polymeric drug 4 as a tan solid. A small sample is dried (50° C./0.1 mm/18 hours) and submitted for elemental analysis. This provides a nitrogen content of 6.85 mequiv/g, and a C/N ratio (mequiv/g basis) of 7.53 (7.50 in theory). Anal. Calcd for $(C_{15}H_{11}N_2O_3Na)_n$: C, 62.07; H, 3.79; N, 9.66. Found: C, 61.93; H, 4.01; N, 9.59.

We claim:

1. A pharmaceutical formulation for the treatment of the mucosa of the mammalian lower intestinal tract comprising an amount therapeutically effective for such treatment of a polymeric compound which itself comprises a pharmacologically acceptable organic polymer backbone comprising a plurality of aromatic rings and having a molecular size which precludes the backbone's absorption from the intestinal lumen and a plurality of salicyclic acid or pharmaceutically acceptable salicylate salt groups covalently bonded to said backbone via azo groups that are intermediate backbone aromatic carbons and said salicyclic acid or pharmaceutically acceptable salicylate salt 5-position carbons in association with a pharmaceutically acceptable carrier therefor.

2. The formulation of claim 1 wherein in said polymeric compound said backbone has an average molecular weight which is not less than 1000 daltons.

3. The formulation of claim 2 wherein in said polymeric compound said plurality of aromatic rings is 10 or greater and said plurality of salicylic acid or salicylate salt groups is 5 or greater.

4. The formulation of claim 3 wherein in said polymeric compound said aromatic rings are pendant from an organic chain which links them together into the polymer backbone.

5. The formulation of claim 3 wherein in said polymeric compound said aromatic rings are present as integral structural units in the organic backbone chain.

6. The formulation of claim 3 wherein said polymeric compound has recurring units of the structure

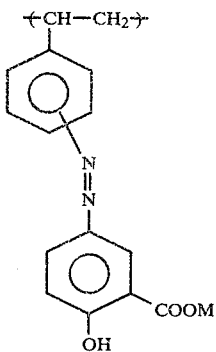

wherein M is hydrogen or a pharmaceutically acceptable cation.

7. The formulation of claim 6 wherein in said polymeric compound M is selected from among hydrogen, potassium and sodium.

8. The formulation of claim 7 wherein in said polymer compound M is potassium.

9. The formulation of claim 7 wherein in said polymeric compound M is sodium.

10. The formulation of claim 3 wherein in said polymeric compound said backbone is poly(vinylamine) and said compound comprises recurring structural units of the formula

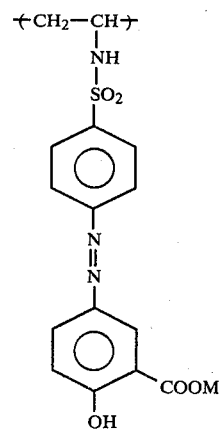

wherein M is hydrogen or a pharmaceutically acceptable cation.

11. The formulation of claim 3 wherein said polymeric compound has recurring units of the structure

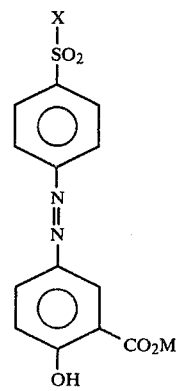

wherein X is an amine group present in poly(ethyleneimine) and M is hydrogen or a pharmaceutically acceptable cation.

12. The formulation of claim 11 wherein in said polymeric compound M is selected from among hydrogen, sodium and potassium.

13. A pharmaceutical formulation for the treatment of the mucosa of the mammalian lower intestinal tract comprising an amount therapeutically effective for such treatment of a polymeric compound itself consisting essentially of from about 250 to about 1500 repeating

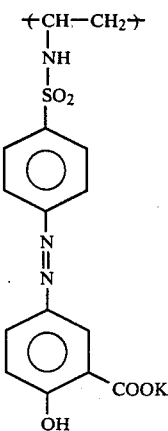

units in association with a pharmaceutically acceptable carrier therefor.

14. A pharmaceutical formulation for the treatment of the mucosa of the mammalian lower intestinal tract comprising an amount therapeutically effective for such treatment of a polymeric compound itself consisting esstentially of from about 250 to about 1500 repeating

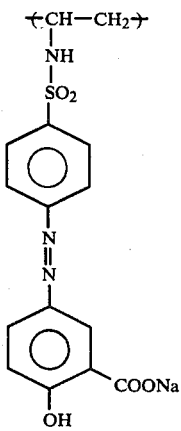

units in association with a pharmaceutically acceptable carrier therefor.

15. A pharmaceutical formulation for the treatment of the mucosa of the mammalian lower intestinal tract comprising an amount therapeutically effective for such treatment of a polymer compount itself consisting essentially of about 1100 repeating

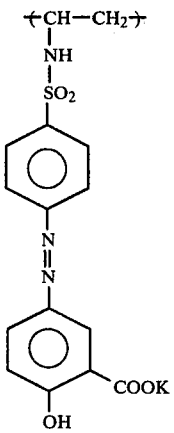

units in association with a pharmaceutically acceptable carrier therefor.

16. A pharmaceutical formulation for the treatment of the mucosa of the mammalian lower intestinal tract comprising an amount therapeutically effective for such treatment of a polymeric component itself consisting essentially of about 1100 repeating

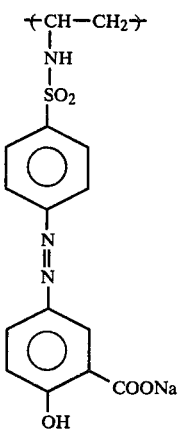

units in association with a pharmaceutically acceptable carrier therefor.

17. A pharmaceutical anti-inflammatory formulation comprising a polymeric compound which itself comprises a pharmacologically acceptable organic polymer backbone comprising a plurality of aromatic rings and having a molecular size which precludes the backbone's absorption from the intestinal lumen and a plurality of salicylic acid or pharmaceutically acceptable salicylate salt groups covalently bonded to said backbone via azo groups that are intermediate backbone aromatic carbons and said salicylic acid or pharmaceutically acceptable salicylate salt 4-position carbons in association with a pharmaceutically acceptable carrier therefor, said polymeric compound being present in an amount effective to release a nontoxic therapeutic anti-inflammatory amount of said salicylic acid or salicylate salts.

18. The anti-inflammatory formulation of claim 17 wherein said polymeric compound has recurring units of the structure

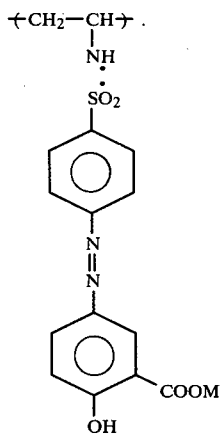

wherein M is selected from among hydrogen, potassium and sodium.

19. A pharmaceutical anti-inflammatory formulation comprising an effective nontoxic inflammation-treating amount of a polymeric compound itself consisting essentially of from about 250 to about 1500 repeating

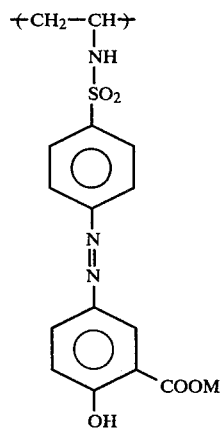

units wherein M is selected from among sodium, potassium and hydrogen in association with a pharmaceutically acceptable carrier therefor.

20. A pharmaceutical formulation for the treatment of ulcerative colitis comprising a polymeric compound which itself comprises a pharmacologically acceptable organic polymer backbone comprising a plurality of aromatic rings and having a molecular size which precludes the backbone's absorption from the intestinal lumen and a plurality of salicylic acid or pharmaceutically acceptable salicylate salt groups covalently bonded to said backbone via azo groups that are intermediate backbone aromatic carbons and said salicylic acid or pharmaceutically acceptable salicylate salt 5-position carbons in association with a pharmaceutically acceptable carrier therefor, said polymeric compound being present in an amount effective to release an ulcerative colitis-treating amount of said salicylic acid or salicylate salt.

21. The pharmaceutical formulation for the treatment of ulcerative colitis of claim 20 wherein said polymeric compound has recurring units of the structure

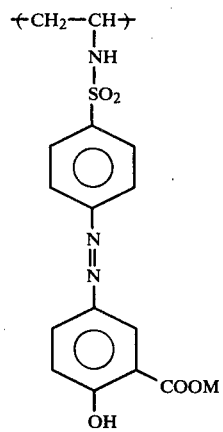

wherein M is selected from among hydrogen, potassium and sodium

22. A pharmaceutical ulcerative-colitis-treating formulation comprising an effective nontoxic ulcerative-colitis-treating amount of a polymeric compound itself consisting essentially of from about 250 to about 1500 repeating

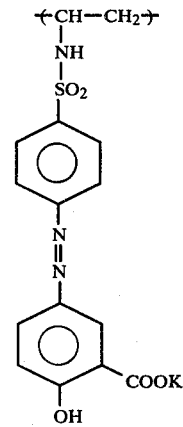

units in association with a pharmaceutically acceptable carrier therefor.

23. A pharmaceutical ulcerative-colitis-treating formulation comprising an effective nontoxic ulcerative-colitis-treating amount of a polymeric compound itself consisting essentially of from about 250 to about 1500 repeating

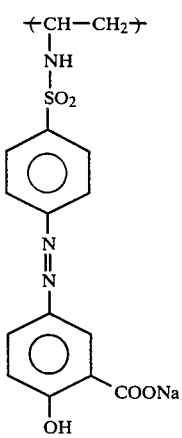

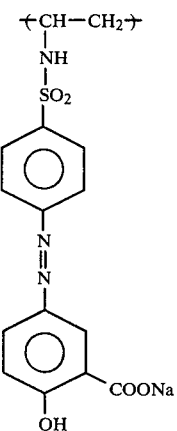

units in association with a pharmaceutically acceptable carrier therefor.

24. The formulation of claim 1 suited for administration by a route selected from oral and rectal.

25. The formulation of claim 7 suited for administration by a route selected from oral and rectal.

26. The formulation of claim 16 suited for administration by a route selected from oral and rectal.

27. The formulation of claim 19 suited for administration by a route selected from oral and rectal.

28. The formulation of claim 23 suited for administration by a route selected from oral and rectal.

29. The formulation of claim 1 in unit dosage form suited for administration by a route selected from oral and rectal.

30. The formulation of claim 29 in unit dosage form selected from suppositories, pills, tablets, and capsules.

31. The formulation of claim 14 in unit dosage form suited for administration by a route selected from oral and rectal.

32. The formulation of claim 19 in unit dosage form suited for administration by a route selected from oral and rectal.

33. The formulation of claim 23 in unit dosage form suited for oral administration.

34. The formulation of claim 23 in unit dosage form suited for rectal administration.

35. A method for the treatment of ulcerative colitis in a mammal which comprises the oral administration to the mammal of an effective nontoxic ulcerative-colitis-treatment amount of a pharmaceutical preparation containing a polymeric compound itself consisting essentially of from about 250 to about 1500 repeating units and a pharamaceutically acceptable carrier therefor.

36. A method for the treatment of ulcerative colitis in a mammal which comprises the rectal administration to the mammal of a nontoxic ulcerative-colitis-treating amount of a pharmaceutical preparation containing a polymeric compound itself consisting essentially of from about 250 to about 1500 repeating

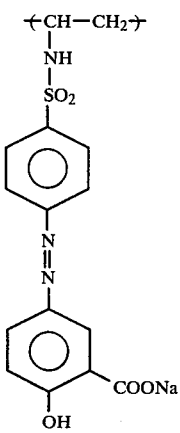

units and a pharamaceutically acceptable carrier therefor.

37. A method for delivering to a mammal a therapeutically effective amount of 5-aminosalicylic acid or its pharmacologically acceptable salts which comprises orally or rectally administering to said mammal an effective amount of the formulation of claim 1.

38. A method for delivering to a mammal a therapeutically effective ulcerative-colitis-treating amount of 5-aminosalicylic acid or its pharmaceutically acceptable salts which comprises orally or rectally administering to said mammal an effective amount of the formulation of claim 23.

* * * * *